(12) United States Patent
Nakayama et al.

(10) Patent No.: US 9,541,516 B2
(45) Date of Patent: Jan. 10, 2017

(54) ELECTROLYTE SOLUTION, METHOD FOR PRODUCING ELECTROLYTE SOLUTION, AND ELECTROCHEMICAL DEVICE

(71) Applicant: Sony Corporation, Tokyo (JP)

(72) Inventors: Yuri Nakayama, Kanagawa (JP);
Hideki Kawasaki, Kyoto (JP);
Hiroyuki Morioka, Kanagawa (JP)

(73) Assignee: Sony Corporation, Tokyo (JP)

( * ) Notice: Subject to any disclaimer, the term of this patent is extended or adjusted under 35 U.S.C. 154(b) by 52 days.

(21) Appl. No.: 14/034,157

(22) Filed: Sep. 23, 2013

(65) Prior Publication Data
US 2014/0127594 A1 May 8, 2014

(30) Foreign Application Priority Data

Sep. 28, 2012 (JP) ................. 2012-216811

(51) Int. Cl.
*H01M 6/16* (2006.01)
*G01N 27/26* (2006.01)
*H01G 9/035* (2006.01)
*H01M 8/02* (2016.01)
*H01M 10/054* (2010.01)
*H01M 10/0568* (2010.01)
*H01M 10/0569* (2010.01)
*H01M 12/08* (2006.01)

(52) U.S. Cl.
CPC ............. *G01N 27/26* (2013.01); *H01G 9/035* (2013.01); *H01M 8/02* (2013.01); *H01M 10/054* (2013.01); *H01M 10/0568* (2013.01); *H01M 10/0569* (2013.01); *H01M 12/08* (2013.01); *H01M 2300/0037* (2013.01)

(58) Field of Classification Search
CPC ...... G01N 27/26; H01G 9/035; H01M 10/054; H01M 10/0568; H01M 10/0569; H01M 12/08; H01M 2300/0037; H01M 8/02
See application file for complete search history.

(56) References Cited

U.S. PATENT DOCUMENTS

2003/0059684 A1* 3/2003 Takami ................. H01M 4/381
429/326
2012/0126231 A1* 5/2012 Momo .................. H01G 11/08
257/53

FOREIGN PATENT DOCUMENTS

| JP | 2003-100347 | 4/2003 |
| JP | 2003-100347 A | 4/2003 |
| JP | 2003-512704 A | 4/2003 |
| JP | 2003-249267 | 9/2003 |
| JP | 2009-021085 A | 1/2009 |
| JP | 2009-093983 | 4/2009 |
| WO | 2013/015369 | 1/2013 |

OTHER PUBLICATIONS

Kim et al., "Structure and compatibility of a magnesium electrolyte with a sulphur cathode", Nature Communications, Macmillan Publishers Limited, Aug. 9, 2011, 6 pages.
Arthur et al., "Electrodeposited Bi, Sb and Bi1-xSbx alloys as anodes for Mg-ion batteries", Electrochemistry Communications 16, Elsevier B.V., Dec. 20, 2011, 4 pages.

* cited by examiner

*Primary Examiner* — Patrick Ryan
*Assistant Examiner* — Ben Lewis
(74) *Attorney, Agent, or Firm* — Chip Law Group

(57) ABSTRACT

There is provided an electrolyte solution including a solvent formed from a sulfone, and a magnesium salt dissolved in the solvent.

18 Claims, 20 Drawing Sheets

ELECTROLYTE SOLUTION, METHOD FOR PRODUCING ELECTROLYTE SOLUTION, AND ELECTROCHEMICAL DEVICE

BACKGROUND

The present disclosure relates to an electrolyte solution, a method for producing an electrolyte solution, and an electrochemical device. More specifically, the present disclosure relates to a suitable electrolyte solution, and method for producing that electrolyte solution, that is used as the electrolyte layer in a magnesium (Mg) ion battery for example, and various electrochemical devices having a magnesium ion battery and the like that uses this electrolyte solution.

Magnesium ion batteries are drawing attention as a next-generation secondary battery to replace lithium ion batteries due to the fact that compared with lithium, magnesium is a much more abundant natural resource and is far cheaper, the amount of electricity per unit volume that can be extracted by a redox reaction is large, and there is also a high level of safety when used in a battery.

In the past, magnesium electrolyte solutions for a magnesium ion battery have all used an ether solvent. Especially, it has been reported that the electrolyte solutions that use tetrahydrofuran (THF) have the best properties (refer to JP-T-2003-512704, JP-A-2009-21085, and Nature Communications Volume: 2, Article number: 427 DOI: doi:10.1038/ncomms1435).

However, ether solvents such as THF are difficult to handle due to their high volatility and because they are often toxic. Further, the potential window (the maximum voltage that can be applied without the electrolyte solution degrading) of a magnesium electrolyte solution that uses an ether solvent is at most about 3.0 V, which is small. Consequently, it has not been possible to produce a battery having a high voltage using a magnesium metal negative electrode.

Due to the above reasons, development has proceeded on magnesium electrolyte solutions that use a solvent other than THF. As a result, a magnesium electrolyte solution was discovered that can be used on magnesium alloy (refer to Electrochemistry Communications 16 (2012) 103-106).

JP-A-2003-100347 discloses a non-aqueous electrolyte battery that uses alkyl sulfone, which is a non-ether solvent, for the electrolyte solution. Specifically, this non-aqueous electrolyte battery includes a positive electrode, a negative electrode including at least one element selected from aluminum, calcium, and magnesium, and a non-aqueous electrolyte solution. This non-aqueous electrolyte solution contains an alkyl sulfone represented by $R_1R_2SO_2$ (wherein $R_1$ and $R_2$ represent an alkyl group) and at least one selected from an aluminum salt, a calcium salt, and a magnesium salt in a mixed solvent of the alkyl sulfone and an organic solvent that dissolves the at least one selected from an aluminum salt, a calcium salt, and a magnesium salt. As the organic solvent, at least one selected from γ-butyrolactone, acetonitrile, and propylene carbonate is used.

SUMMARY

However, in JP-T-2003-512704 there is no description about whether the disclosed non-aqueous electrolyte solution can be used on magnesium metal or whether it exhibits an electrochemically reversible precipitation/dissolution reaction of magnesium. Therefore, irrespective of JP-T-2003-512704, it can be said that the only electrolyte solutions capable of being used on magnesium metal still use an ether solvent.

Therefore, according to an embodiment of the present disclosure, there is provided an electrolyte solution, and a method for producing that electrolyte solution, that uses a non-ether solvent, can be used on magnesium metal, and can exhibit an electrochemically reversible precipitation/dissolution reaction of magnesium.

According to another embodiment of the present disclosure, there is provided an electrochemical device having a battery and the like that uses such an excellent electrolyte solution.

The above-described problems as well as other issues with become clear based on the following descriptions in the present specification with reference to the attached drawings.

As a result of diligent research to resolve the above problems, the present inventors discovered that an electrolyte solution in which a magnesium salt has been dissolved in a solvent formed from a sulfone, or an electrolyte solution in which a magnesium salt has been dissolved in a solvent formed from a sulfone and a non-polar solvent, is effective as an electrolyte solution that can be used on a magnesium metal. Further, the present inventors actually confirmed for magnesium metal that such an electrolyte solution exhibits a reversible precipitation/dissolution reaction of magnesium, thereby arriving at the present disclosure. To the extent of the present inventors' knowledge, there have been no reports in the past of a magnesium electrolyte solution that uses a sulfone solvent which exhibits an electrochemically reversible precipitation/dissolution reaction of magnesium.

According to an embodiment of the present disclosure, there is provided an electrolyte solution including a solvent formed from a sulfone, and a magnesium salt dissolved in the solvent.

This electrolyte solution is a magnesium ion-containing non-aqueous electrolyte solution that contains magnesium ions due to the dissolution of a magnesium salt in a sulfone. This electrolyte solution typically contains a magnesium complex that has a four-coordinate dimer structure in which the sulfone is coordinated to the magnesium.

The sulfone is typically an alkyl sulfone or an alkyl sulfone derivative represented by $R_1R_2SO_2$ (wherein $R_1$ and $R_2$ represent an alkyl group). Here, the kind (the number and combination of carbon atoms) of $R_1$ and $R_2$ is not especially limited, and may be selected as appropriate. The number of carbon atoms of $R_1$ and $R_2$ is preferably, although not limited to, 4 or less. Further, the sum of the number of $R_1$ carbon atoms and the number of $R_2$ carbon atoms is preferably, although not limited to, 4 or more to 7 or less. Examples of $R_1$ and $R_2$ include a methyl group, an ethyl group, an n-propyl group, an i-propyl group, an n-butyl, an i-butyl, an s-butyl group, a t-butyl group and the like. Specific examples of the alkyl sulfone include at least one selected from the group consisting of dimethyl sulfone (DMS), methyl ethyl sulfone (MES), methyl-n-propyl sulfone (MnPS), methyl-i-propyl sulfone (MiPS), methyl-n-butyl sulfone (MnBS), methyl-i-butyl sulfone (MiBS), methyl-s-butyl sulfone (MsBS), methyl-t-butyl sulfone (MtBS), ethyl methyl sulfone (EMS), diethyl sulfone (DES), ethyl-n-propyl sulfone (EnPS), ethyl-i-propyl sulfone (EiPS), ethyl-n-butyl sulfone (EnBS), ethyl-i-butyl sulfone (EiBS), ethyl-s-butyl sulfone (EsBS), ethyl-t-butyl sulfone (EtBS), di-n-propyl sulfone (DnPS), di-i-propyl sulfone (DiPS), n-propyl-n-butyl sulfone (nPnBS), n-butyl ethyl sulfone (nBES), i-butyl ethyl sulfone (iBES), s-butyl ethyl sulfone (sBES), and di-n-butyl sulfone (DnBS). Examples of the alkyl sulfone derivative include ethyl phenyl sulfone (EPhS).

Examples of the magnesium salt include at least one selected from the group consisting of magnesium chloride ($MgCl_2$), magnesium bromide ($MgBr_2$), magnesium iodide ($MgI_2$), magnesium perchlorate ($Mg(ClO_4)_2$), magnesium tetrafluoroborate ($Mg(BF_4)_2$), magnesium hexafluorophosphate ($Mg(PF_6)_2$), magnesium hexafluoroarsenate ($Mg(AsF_6)_2$), magnesium perfluoroalkyl sulfonate ($(Rf1SO_3)_2$; MgRf1 is a perfluoroalkyl group), and magnesium perfluoroalkylsulfonyl imidate ($Mg((Rf2SO_2)_2N)_2$; Rf2 is a perfluoroalkyl group). Among these magnesium salts, $MgX_2$ (wherein X=Cl, Br, or I) is especially preferred.

The electrolyte solution can optionally contain an additive. This additive is, for example, a salt formed from a cation in which the metal ion is at least one atom or group of atoms selected from the group consisting of aluminum (Al), beryllium (Be), boron (B), gallium (Ga), indium (In), silicon (Si), tin (Sn), titanium (Ti), chromium (Cr), iron (Fe), cobalt (Co), and lanthanum (La). Alternatively, the additive may be a salt formed from at least one atom, organic group, or anion selected from the group consisting of hydrogen, an alkyl group, an alkenyl group, an aryl group, a benzyl group, an amide group, a fluoride ion ($F^-$), a chloride ion ($Cl^-$), a bromide ion ($Br^-$), an iodide ion ($I^-$), a perchlorate ion ($ClO4^-$), a tetrafluoroborate ion ($BF_4^-$), a hexafluorophosphate ion ($PF_6^-$), a hexafluoroarsenate ion ($AsF_6^-$), a perfluoroalkyl sulfonate ion ($Rf1SO_3^-$; Rf1 is a perfluoroalkyl group), and a perfluoroalkylsulfonyl imide ion ($(Rf2SO_2)_2N^-$; Rf2 is a perfluoroalkyl group). By adding such an additive, the ion coinductivity of the electrolyte solution can be improved.

According to an embodiment of the present disclosure, there is provide a method for producing an electrolyte solution, the method including dissolving a magnesium salt in a low-boiling-point solvent capable of dissolving a magnesium salt, dissolving a sulfone in a solution in which the magnesium salt is dissolved in the low-boiling-point solvent, and removing the low-boiling-point solvent from the solution in which the sulfone is dissolved.

As the low-boiling-point solvent capable of dissolving the magnesium salt, basically any solvent that can dissolve the magnesium salt and has a boiling point lower than the selected sulfone can be used. Although this solvent is selected as appropriate, it is preferred to use an alcohol. The alcohol may be a monohydric alcohol or a polyhydric alcohol, and may be a saturated alcohol or an unsaturated alcohol. Specific examples of the alcohol include, but are not limited to, methanol, ethanol, 1-propanol, 2-propanol (isopropanol), 1-butanol, 2-butanol (sec-butanol), 2-methyl-1-propanol (isobutanol), 2-methyl-2-propanol (tert-butanol), and 1-pentanol.

Further, according to an embodiment of the present disclosure, there is provided an electrolyte solution including a solvent formed from a sulfone and a non-polar solvent, and a magnesium salt dissolved in the solvent.

The non-polar solvent is to be selected as necessary; however, it is preferably a non-aqueous solvent having a permittivity and a donor number that are both 20 or less. Specifically, the non-polar solvent is at least one selected from the group consisting of an aromatic hydrocarbon, an ether, a ketone, an ester, and a chain carbonate. The aromatic hydrocarbon is toluene, benzene, o-xylene, m-xylene, p-xylene, or 1-methyl naphthalene, the ether is diethyl ether or tetrahydrofuran, the ketone is 4-methyl-2-pentanone, the ester is methyl acetate or ethyl acetate, and the chain carbonate is dimethyl carbonate, diethyl carbonate, or ethyl methyl carbonate.

The sulfone and the magnesium salt are the same as described above. Further, the same additives as described above may be added to the electrolyte solution as appropriate.

According to an embodiment of the present disclosure, there is provide a method for producing an electrolyte solution, the method including dissolving a magnesium salt in a low-boiling-point solvent capable of dissolving a magnesium salt, dissolving a sulfone in the solution in which the magnesium salt is dissolved in the low-boiling-point solvent, removing the low-boiling-point solvent from the solution in which the sulfone is dissolved, and mixing a non-polar solvent in the solution from which the low-boiling-point solvent was removed.

The sulfone, the magnesium salt, and the low-boiling-point solvent are the same as described above.

According to an embodiment of the present disclosure, there is provide an electrochemical device including an electrolyte solution. The electrolyte solution is an electrolyte solution including a solvent formed from a sulfone and a magnesium salt dissolved in the solvent, or an electrolyte solution including a solvent formed from a sulfone and a non-polar solvent, and a magnesium salt dissolved in the solvent.

Although the electrochemical device may basically be any device, specific examples include various magnesium-using batteries, capacitors, sensors, magnesium ion filters and the like. Examples of magnesium-using batteries include secondary batteries, air batteries, fuel cells and the like. Secondary batteries are, for example, a magnesium ion battery that has the above-described electrolyte solution as an electrolyte layer.

Further, according to an embodiment of the present disclosure, there is provided a battery pack including:

a secondary battery;

a control unit configured to perform controls relating to the secondary battery; and a casing configured to enclose the secondary battery, wherein the secondary battery has an electrolyte solution, and wherein the electrolyte solution is an electrolyte solution having a solvent formed from a sulfone and a magnesium salt dissolved in the solvent, or an electrolyte solution having a solvent formed from a sulfone and a non-polar solvent, and a magnesium salt dissolved in the solvent.

In this battery pack, the control unit controls, for example, charging/discharging, over discharging, or over charging of the secondary battery.

Further, according to an embodiment of the present disclosure, there is provided an electronic device configured to receive a supply of power from a secondary battery including an electrolyte solution, wherein the electrolyte solution is an electrolyte solution having a solvent formed from a sulfone and a magnesium salt dissolved in the solvent, or an electrolyte solution having a solvent formed from a sulfone and a non-polar solvent, and a magnesium salt dissolved in the solvent.

Further, according to an embodiment of the present disclosure, there is provided an electric vehicle including:

a conversion apparatus configured to receive a supply of power from a secondary battery and convert the received power into a vehicle drive force; and a control apparatus configured to perform information processing relating to vehicle control based on information relating to the secondary battery, wherein the secondary battery has an electrolyte solution, and wherein the electrolyte solution is an electrolyte solution having a solvent formed from a sulfone and a magnesium salt dissolved in the solvent, or an electrolyte solution having a solvent formed from a sulfone and a non-polar solvent, and a magnesium salt dissolved in the solvent.

In this electric vehicle, the conversion apparatus typically generates a drive force by receiving a supply of power from the secondary battery and rotating a motor. This motor can utilize regenerative energy. Further, the control apparatus performs information processing relating to vehicle control based on, for example, the remaining battery level of the secondary battery. Examples of the electric vehicle include, in addition to electric automobiles, electric motorbikes, electric bicycles, railroad wagons and the like, so-called hybrid automobiles.

Further, according to an embodiment of the present disclosure, there is provided a power system configured to receive a supply of power from a secondary battery and/or supply power from a power source to a secondary battery, wherein the secondary battery includes an electrolyte solution, and wherein the electrolyte solution is an electrolyte solution having a solvent formed from a sulfone and a magnesium salt dissolved in the solvent, or an electrolyte solution having a solvent formed from a sulfone and a non-polar solvent, and a magnesium salt dissolved in the solvent.

This power system can be any system, including a simple power apparatus, as long as the system uses electric power. Examples of the power system, which can also store power, include a smart grid, a household energy management system (HEMS), vehicles and the like.

Further, according to an embodiment of the present disclosure, there is provided a power storage power source configured so that an electronic device to which power is supplied is connected, the power storage power source including a secondary battery, wherein the secondary battery has an electrolyte solution, and wherein the electrolyte solution is an electrolyte solution having a solvent formed from a sulfone and a magnesium salt dissolved in the solvent, or an electrolyte solution having a solvent formed from a sulfone and a non-polar solvent, and a magnesium salt dissolved in the solvent.

The applications of this power storage power source are not limited, basically the power storage power source can be used in any power system or power apparatus. For example, the power storage power source can be used in a smart grid.

According to the embodiments of the present disclosure described above, an electrolyte solution that uses a sulfone, which is a non-ether solvent, can be obtained that can be used on magnesium metal and exhibits an electrochemically reversible precipitation/dissolution reaction. Further, by using this excellent electrolyte solution for an electrolyte layer, a high-performance electrochemical device having a magnesium ion battery and the like can be realized.

DETAILED DESCRIPTION OF THE EMBODIMENT(S)

Figure 1:
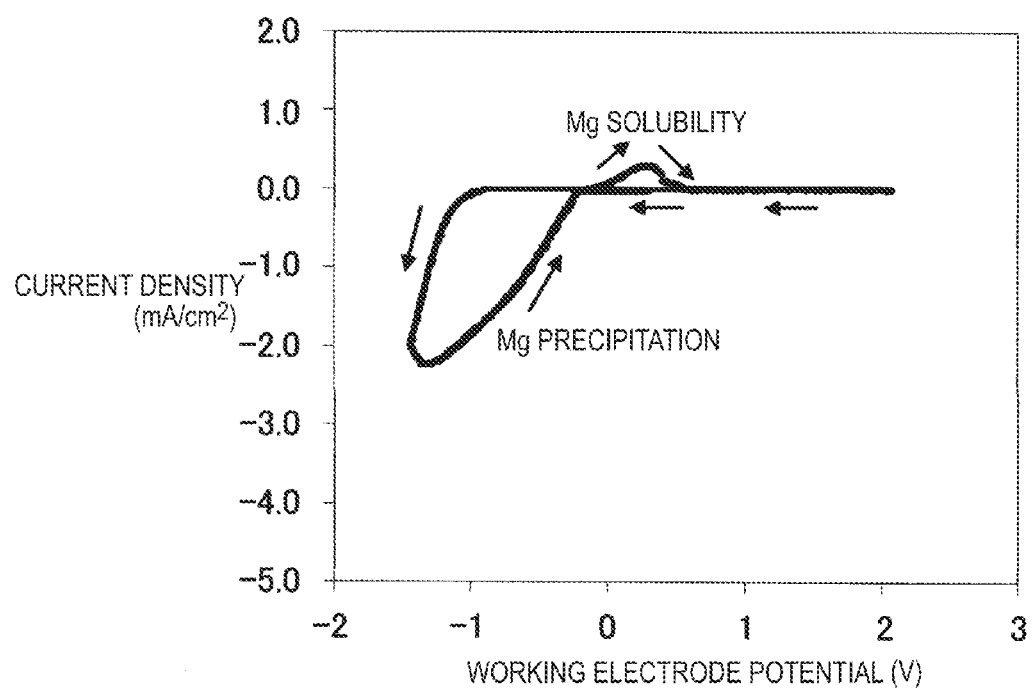
FIG. 1 is a graph illustrating a CV measurement result of the electrolyte solution of Working Example 1.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Embodiments for carrying out the present technology (hereinafter referred to as "embodiments of the present disclosure" will now be described in the following order.

1. First embodiment of the present disclosure (electrolyte solution and production method thereof)

2. Second embodiment of the present disclosure (electrolyte solution and production method thereof)

3. Third embodiment of the present disclosure (magnesium ion battery)

1. First Embodiment of the Present Disclosure

Electrolyte Solution

The electrolyte solution according to the first embodiment of the present disclosure is a magnesium ion-containing non-aqueous electrolyte solution in which a magnesium salt is dissolved in a solvent formed from a sulfone. The sulfone and the magnesium salt may be selected from among the examples mentioned above, for example. The molar ratio of the sulfone based on the magnesium salt in the electrolyte solution is, for example, 4 or more to 35 or less, typically is 6 or more to 16 or less, and preferably is 7 or more to 9 or less. However, the molar range is not limited to these ranges. The magnesium salt typically includes a magnesium complex that has a four-coordinate dimer structure in which the sulfone is coordinated to the magnesium.
(Method of Producing the Electrolyte Solution)

The electrolyte solution can be produced as follows, for example.

First, the magnesium salt is dissolved in an alcohol. As the magnesium salt, it is preferred to use an anhydrous magnesium salt. Generally, although magnesium salts do not dissolve in sulfones, they do dissolve well in alcohols. When the magnesium salt is thus dissolved in the alcohol, the alcohol coordinates to the magnesium. The alcohol may be selected from among the examples mentioned above, for example. As the alcohol, it is preferred to use a dehydrated alcohol. Next, the sulfone is dissolved in the thus-obtained solution in which the magnesium salt was dissolved in the alcohol. Then, the alcohol is removed by heating this solution under reduced pressure. During this process of removing the alcohol, the alcohol coordinated to the magnesium is exchanged (or substituted) with the sulfone. Based on the above processes, the target electrolyte solution is produced.

According to this first embodiment of the present disclosure, a magnesium ion-containing non-aqueous electrolyte solution can be obtained that can be used on magnesium metal and exhibits a precipitation/dissolution reaction that is electrochemically reversible at room temperature using a sulfone, which is a non-ether solvent. The sulfone that is used for the solvent generally has a higher boiling point than an ether solvent like THF, and thus has a low volatility and is highly safe. Accordingly, the electrolyte solution can be easily handled, which consequently allows the processes when producing a magnesium ion battery, for example, to be greatly simplified. Further, since the electrolyte solution has a wider potential window than past magnesium electrolyte solutions that use THF as a solvent, there is a wider range of choices for the positive electrode material of the magnesium secondary battery, and the voltage, namely the energy density, of the realizable secondary battery can be improved. In addition, since this electrolyte solution has a simple composition, the costs of the electrolyte solution itself can be substantially reduced.

2. Second Embodiment of the Present Disclosure

Electrolyte Solution

The electrolyte solution according to the second embodiment of the present disclosure is a magnesium ion-containing non-aqueous electrolyte solution in which a magnesium salt is dissolved in a solvent formed from a sulfone and a non-polar solvent. The sulfone, non-polar solvent, and magnesium salt may be selected from among the examples mentioned above, for example. The molar ratio of the sulfone based on the magnesium salt in the electrolyte solution is, for example, 4 or more to 20 or less, typically is 6 or more to 16 or less, and preferably is 7 or more to 9 or less. However, the molar range is not limited to these ranges. The magnesium salt typically includes a magnesium complex that has a four-coordinate dimer structure in which the sulfone is coordinated to the magnesium.
(Method of Producing the Electrolyte Solution)

The electrolyte solution can be produced as follows, for example.

First, the magnesium salt is dissolved in an alcohol. As a result, the alcohol coordinates to the magnesium. As the magnesium salt, it is preferred to use an anhydrous magnesium salt. The alcohol may be selected from among the examples mentioned above, for example. Next, the sulfone is dissolved in the thus-obtained solution in which the magnesium salt was dissolved in the alcohol. Then, the alcohol is removed by heating this solution under reduced pressure. During this process of removing the alcohol, the alcohol coordinated to the magnesium is exchanged with the sulfone. After this, the non-polar solvent is admixed into the solution from which the alcohol was removed. The non-polar solvent may be selected from among the examples mentioned above, for example. Based on the above processes, the target electrolyte solution is produced.

According to the second embodiment of the present disclosure, the same advantages can be obtained as the first embodiment of the present disclosure.

Working Example 1

A Mg electrolyte solution (Mg-EnPS) was prepared as follows.

Weighing of the reagents and the mixing operation were carried out in a glove box (Ar/dew point −80 to −90° C.). While stirring 100 mL of dehydrated methanol (manufactured by Nacalai Tesque, Inc.) with a stirrer, 3.81 g of anhydrous magnesium chloride (II) ($MgCl_2$) (manufactured by Sigma-Aldrich Co., LLC) was added. It was confirmed by measuring the external temperature of the reaction vessel with a contact thermometer (T2; manufactured by testo K.K.) that a slight amount of heat was produced when the $MgCl_2$ dissolved in the methanol. This heat is generated by the heat of reaction when the methanol coordinates to the Mg. The Mg in the methanol is thought to have a structure in which the methanol is coordinated to it. Further, there was a slight amount of white cloudiness after the dissolution of the $MgCl_2$ as well. This is thought to be due to the water present in the methanol reacting with the Mg to produce $Mg(OH)_2$. Since the white cloudiness was slight, synthesis was continued without filtering.

After dissolution of the $MgCl_2$, 43.6 g of EnPS was added while stirring with a stirrer.

The solution was removed from the glove box while maintaining a state in which air was prevented from mixing therein. Then, while reducing the pressure using a rotary pump (G-110D, manufactured by ULVAC Technologies, Inc.), the methanol was removed by heating and stirring at 120° C. for 2 hours. Although a white sediment was produced when the amount of methanol decreased, the produced sediment dissolved when the pressure reduction and heating were continued. This change in solubility is thought to be due to the exchange of the Mg ligands from methanol to EnPS. The removal of the methanol was confirmed by $^1$H NMR measurement.

Since the white cloudiness produced when the $MgCl_2$ dissolved in the methanol remained in the sample from which methanol had been removed, the sample was filtered (pore size 0.45 μm, manufactured by Whatman Ltd.) in a glove box.

The prepared electrolyte solution had a Mg:Cl:EnPS ratio of 1:2:8 (molar ratio) and a Mg concentration of 0.95 mol/L.

Working Example 2

A Mg electrolyte solution (Mg-EnPS-toluene) was prepared as follows.

Weighing of the reagents and the mixing operation were carried out in a glove box (Ar/dew point −80 to −90° C.). While stirring 11.8 g of the electrolyte solution of Working Example 1 (Mg-EnPS) with a stirrer, 1.9 g of low-moisture toluene (manufactured by Nacalai Tesque, Inc.) was added.

The prepared electrolyte solution had a Mg:Cl:EnPS ratio of 1:2:8 (molar ratio), a $MgCl_2$:toluene ratio of 1:2 (molar ratio), and a Mg concentration of 0.78 mol/L.

Working Example 3

A Mg electrolyte solution (Mg-EnPS-$BF_4$) was prepared as follows.

Weighing of the reagents and the mixing operation were carried out in a glove box (Ar/dew point −80 to −90° C.). While stirring 11.8 g of the electrolyte solution of Working Example 1 (Mg-EnPS) with a stirrer, 3.9 g of $AgBF_4$ (manufactured by Tokyo Chemical Industry Co., Ltd.) (ratio of $MgCl_2$:$AgBF_4$ in the electrolyte solution of 1:2 (molar ratio)) was added. It was confirmed by measuring the external temperature of the reaction vessel with a contact thermometer (T2; manufactured by testo K.K.) that heat was produced when the $AgBF_4$ was added. The $AgBF_4$ was added at a rate at which the temperature of the sample did not exceed 40° C. due to this generation of heat. This heat is generated by the heat of reaction when AgCl is formed. The produced AgCl precipitates. After adding all of the $AgBF_4$ and then stirring for 1 day with a stirrer, the AgCl was removed by filtering (pore size 0.45 μm, manufactured by Whatman Ltd.) with a centrifugal separator (Chibitan II, manufactured by Millipore Corporation) (maximum RCF 5,200×g (51,000 m/s$^2$), 10 min)

The prepared electrolyte solution had a Mg:EnPS ratio of 1:8 (molar ratio), a Mg:$BF_4$ ratio of 1:2 (molar ratio), and a Mg concentration of 0.95 mol/L.

(Electrolyte Solution Cyclic Voltammetry (CV) Measurement)

To examine the electrical properties of the thus-prepared electrolyte solutions of Working Examples 1 to 3, the cyclic voltammetry (CV) of the electrolyte solutions was measured. The measurement was carried out at room temperature using a three electrode cell (amount of electrolyte solution 1 mL), using a platinum (Pt) electrode (diameter 1.6 mm, manufactured by BAS) for the working electrode and a magnesium (Mg) wire (diameter 1.6 mm, manufactured by Nilaco Corporation) for the counter electrode and the reference electrode (Ar/dew point −80 to −90° C.).

Measurement of the first cycle was carried out by, starting from an open circuit state (OCV), changing the voltage in order of OCV→about −1.5 V→about +2.0 V so that at first the potential of the working electrode with respect to the reference electrode was decreased by about 1.5 V to the reduction side, then increased by about 2.0 V to the oxidation side, and finally returned to the OCV. The rate at which the potential was applied was set at 5 mV.

Figure 2:
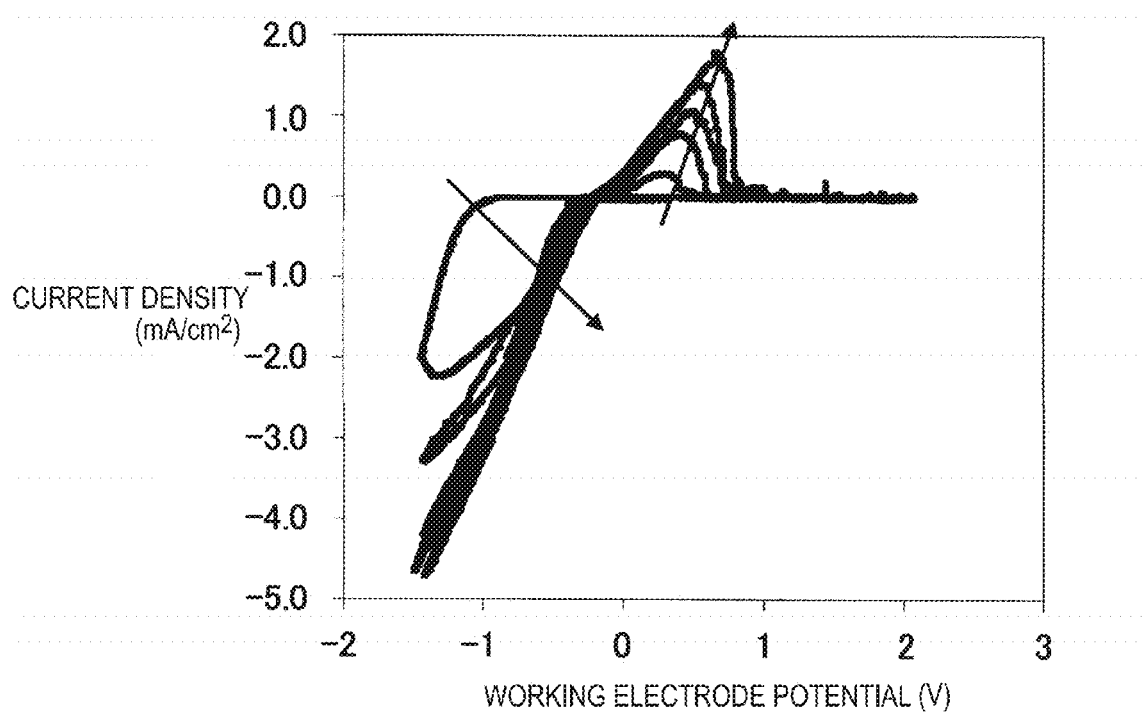
FIG. 2 is a graph illustrating a CV measurement result of the electrolyte solution of Working Example 1.

FIGS. 1 and 2 are graphs illustrating the CV measurement results of the electrolyte solution of Working Example 1 (Mg-EnPS). The horizontal axis in FIGS. 1 and 2 represents the potential of the working electrode versus the potential of the reference electrode. From these graphs it can be seen that an electrolyte solution capable of reversibly dissolving and precipitating Mg can be prepared based on a composition of only $MgCl_2$ and EnPS. From FIG. 2 it can be seen that the larger the cycle number, the greater the current that flows during oxidation and reduction. This is thought to be due to the state of the electrode surface changing. Further, after CV measurement, a black deposit was present on the working electrode and at the lower portion of the working electrode. This is the Mg produced by reduction. The reason why the amount of current on the oxidation side is smaller than the amount of current on the reduction side is thought to be due to Mg produced by reduction peeling from the electrode surface.

Figure 3:
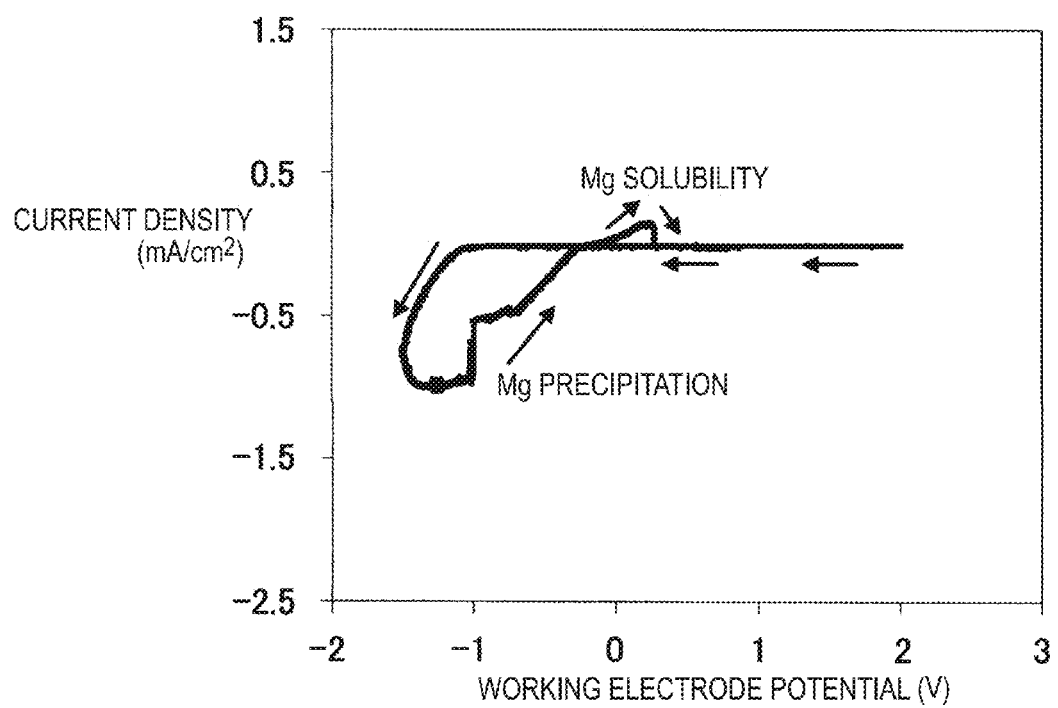
FIG. 3 is a graph illustrating a CV measurement result of the electrolyte solution of Working Example 2.
Figure 4:
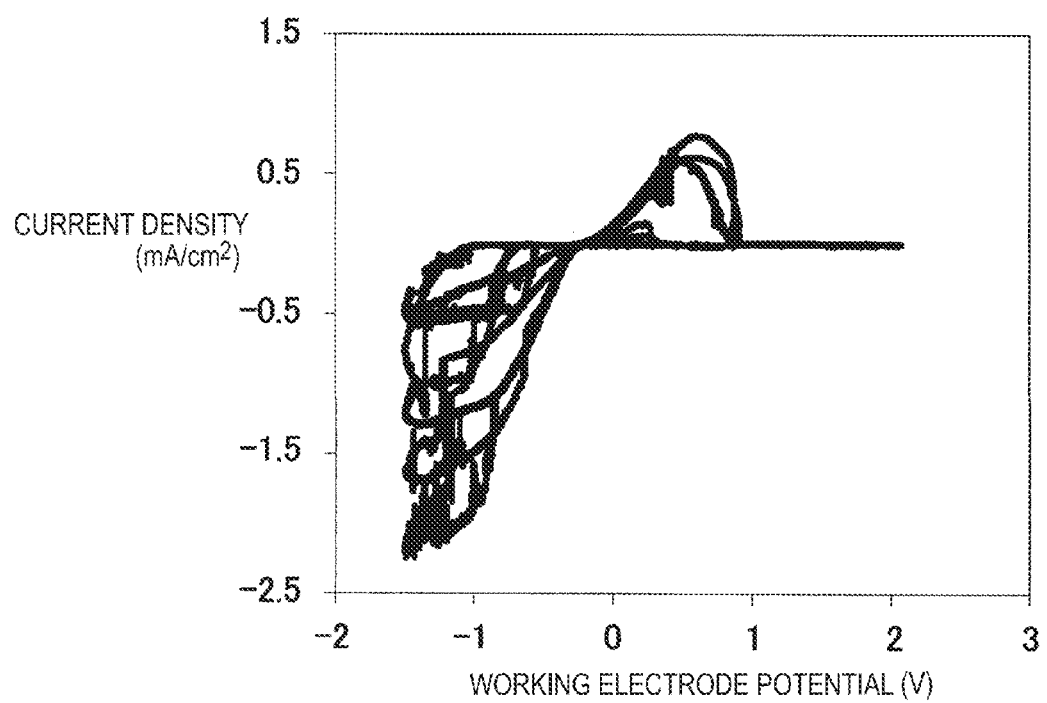
FIG. 4 is a graph illustrating a CV measurement result of the electrolyte solution of Working Example 2.

FIGS. 3 and 4 are graphs illustrating the CV measurement results of the electrolyte solution of Working Example 2 (Mg-EnPS-toluene). It can also be seen from these graphs that an electrolyte solution capable of reversibly dissolving and precipitating Mg can be prepared based on a composition of $MgCl_2$, EnPS, and toluene. From a comparison with FIGS. 1 and 2, it can be seen that the potential at which oxidation and reduction of Mg starts hardly changes even if toluene is added. This suggests that the structure of the Mg complexes relating to oxidation and reduction is similar. However, when toluene is added, despite the fact that the viscosity of the electrolyte solution decreases, the current flowing during oxidation and reduction decreases in both cases. This suggests that adding toluene causes a change in the dissociation state of the electrolyte solution ions. It is noted that a tendency for the current flowing during oxidation and reduction to increase as the cycle number increases like that seen with the electrolyte solution of Working Example 1 (Mg-EnPS) was not seen in FIG. 4. In FIG. 4, a random current value was seen for each cycle.

Figure 5:
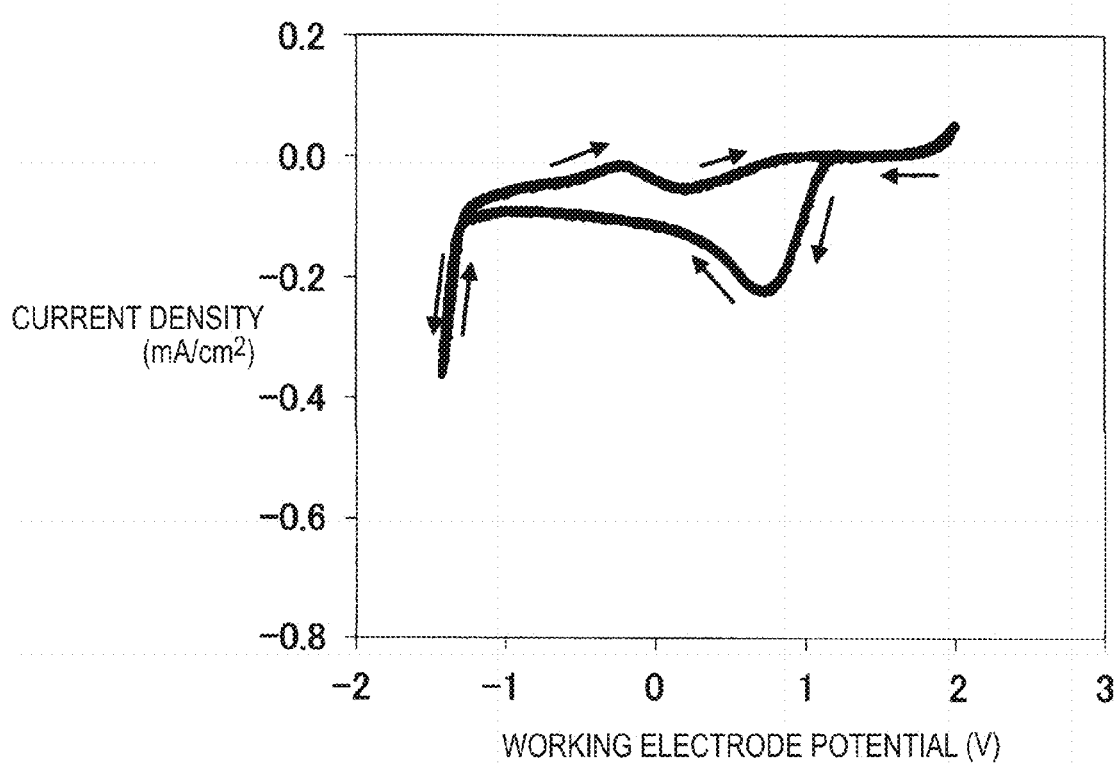
FIG. 5 is a graph illustrating a CV measurement result of the electrolyte solution of Working Example 3.
Figure 6:
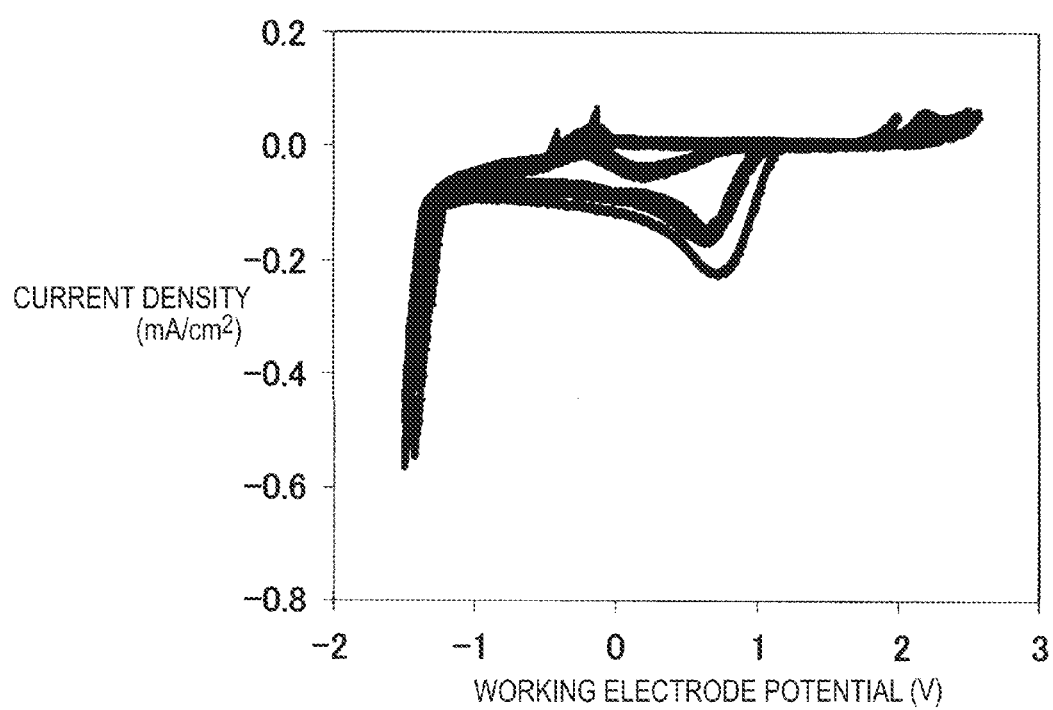
FIG. 6 is a graph illustrating a CV measurement result of the electrolyte solution of Working Example 3.

FIGS. 5 and 6 are graphs illustrating the CV measurement results of the electrolyte solution of Working Example 3 (Mg-EnPS-$BF_4$). From these graphs it can be seen that the electrolyte solution of Working Example 3 exhibits a different waveform to the CV measurement results for the electrolyte solution of Working Example 1 (Mg-EnPS) and the electrolyte solution of Working Example 2 (Mg-EnPS-toluene), thus indicating that a plurality of redox reactions are occurring. This suggests that the structure of the Mg complexes relating to oxidation and reduction in the electrolyte solution of Working Example 3 is different to that of the electrolyte solutions of Examples 1 and 2. Further, considering that only the electrolyte solution of Working Example 3 does not include chlorine, it is highly likely that chlorine plays an important role in the oxidation and reduction behavior confirmed in Working Examples 1 and 2. The remaining Ag used during preparation also has an effect.

Figure 7:
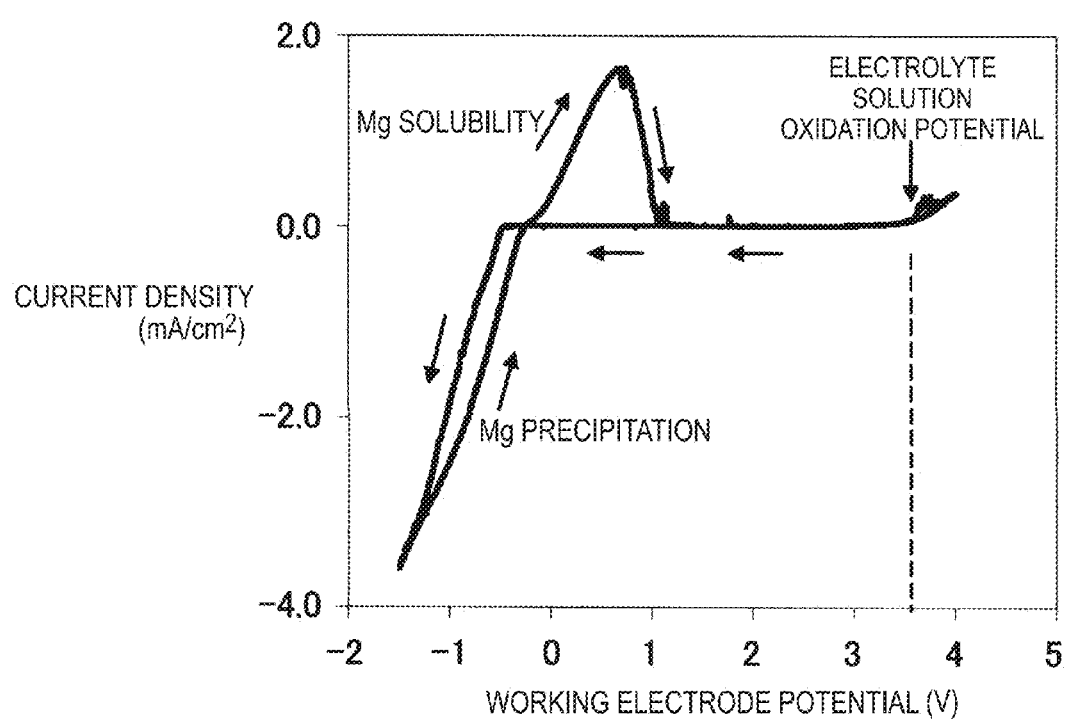
FIG. 7 is a graph illustrating a CV measurement result for examining the oxidation potential at which oxidative degradation of the electrolyte solution of Working Example 1 starts.

FIG. 7 is a graph illustrating a CV measurement result for examining the oxidation potential at which oxidative degradation of the electrolyte solution of Working Example 1 (Mg-EnPS) starts. The rate at which the potential was applied was set at 10 mV. As can be seen from FIG. 7, with the electrolyte solution of Working Example 1 (Mg-EnPS), oxidative degradation occurred when the potential of the working electrode was greater than the potential of the reference electrode by 3.5 V or more.

(¹H NMR Measurement)

The ¹H NMR of the intermediate preparation product of the electrolyte solutions of Working Examples 1 to 3 and of the electrolyte solutions of Working Examples 1 to 3 was measured to examine the coordination of EnPS to magnesium. The ¹H NMR measurement was carried out using the NOVA 400 (400 MHz) manufactured by Varian, Inc. Since the environment of the electrolyte changes if a deuterated solvent is added, the electrolyte solution was measured as a crude solution in situ. Consequently, the measurement was carried out without locking with a deuterated solvent, and the chemical shift was corrected using a separately measured external reference. Deuterated chloroform was used as the external reference. The peak position of the included chloroform that did not turn into a deuterated solvent was 7.26 ppm. A measurement sample was produced by sealing about 0.6 mL in a 5 mm-diameter NMR tube in a glove box (Ar/dew point −80 to −90° C.).

Figure 8:
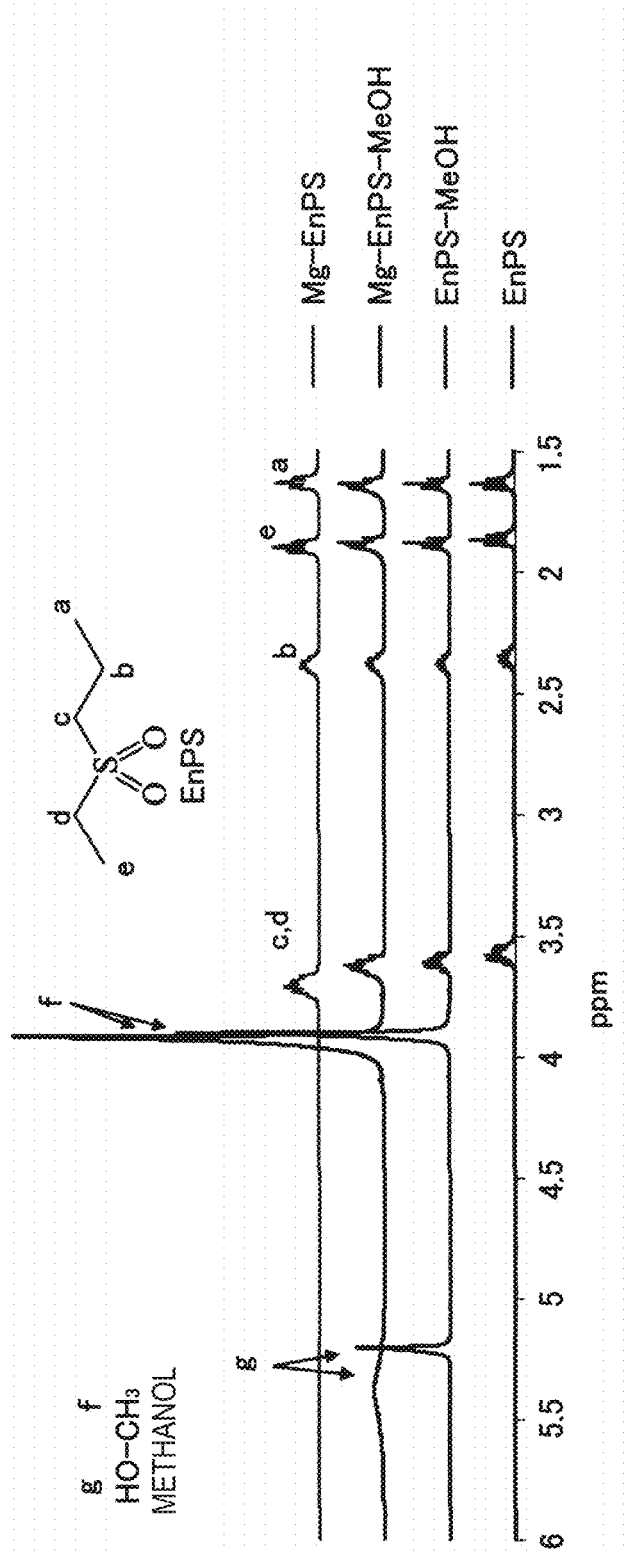
FIG. 8 is a line diagram illustrating the $^1$H NMR spectra of the electrolyte solution of Working Example 1.

FIG. 8 illustrates the ¹H NMR measurement result of the electrolyte solution of Working Example 1 (Mg-EnPS) along with the results for EnPS and for comparison the prepared EnPS-MeOH and Mg-EnPS-MeOH, for the purpose of observing ligand exchange during electrolyte solution preparation. The EnPS-MeOH was a sample in which EnPS and methanol were mixed in the same ratio as during preparation of the electrolyte solution of Working Example 1 (Mg-EnPS), and the Mg-EnPS-MeOH was a sample in which EnPS was added after $MgCl_2$ was dissolved in methanol in the same ratio as during preparation of the electrolyte solution of Working Example 1 (Mg-EnPS). All of the spectra were normalized on both the vertical axis and the horizontal axis based on the peak of the normal propyl end moiety (a in the chemical formula of EnPS illustrated in FIG. 8) in the EnPS that is considered to be the least susceptible to the influence of the coordination to Mg among the EnPS signals.

In FIG. 8, a comparison of the EnPS-MeOH spectra and the spectra of the sample obtained by adding $MgCl_2$ to EnPS-MeOH (Mg-EnPS-MeOH) shows that the peak for the methyl group moiety (f on the methanol illustrated in FIG. 8) on the Mg-EnPS-MeOH methanol has shifted to a lower field, and that the peak for the hydroxyl group moiety (g on the methanol illustrated in FIG. 8) on the Mg-EnPS-MeOH methanol has broadened. This suggests that the methanol is coordinated to the Mg by the OH moiety. Further, since the peak for the hydrogens (c and d in the chemical formula of EnPS illustrated in FIG. 8) closet to the EnPS oxygen has shifted to a slightly lower field, it can also be thought that the EnPS is also coordinated. In addition, since only one of these peaks is observed, it is also thought that the methanol and EnPS underwent ligand exchange at a faster rate than the observation time of the of the NMR.

Next, a comparison of the Mg-EnPS-MeOH spectra and the spectra of a sample obtained by removing the methanol from Mg-EnPS-MeOH (Mg-EnPS) shows that the peak for the hydrogens (c and d in the chemical formula of EnPS illustrated in FIG. 8) closet to the Mg-EnPS oxygen has shifted to a lower field. This suggests that by removing the methanol, there is more EnPS than magnesium, and that the EnPS is more strongly coordinated.

Based on the above, when $MgCl_2$ is dissolved in methanol, the methanol or Cl is coordinated to the magnesium, and by adding EnPS the methanol, the EnPS, and the Cl are coordinated. By removing the methanol from the mixture, the EnPS and the Cl are coordinated to the magnesium.

Figure 9:
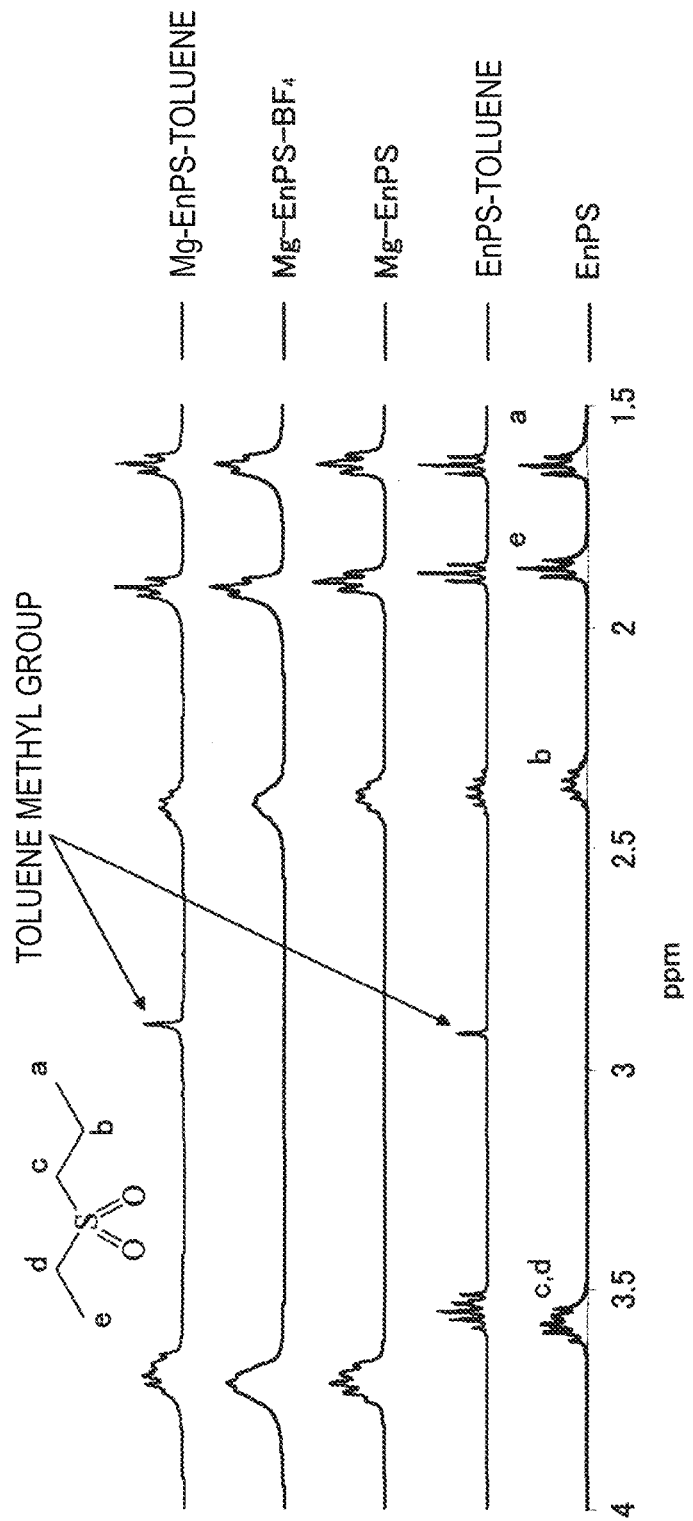
FIG. 9 is a line diagram illustrating the $^1$H NMR spectra of the electrolyte solutions of Working Examples 1 to 3.

FIG. 9 illustrates the ¹H NMR measurement results of the electrolyte solution of Working Example 1 (Mg-EnPS), the electrolyte solution of Working Example 2 (Mg-EnPS-toluene), and the electrolyte solution of Working Example 3 (Mg-EnPS-$BF_4$) along with the results for EnPS and for comparison the prepared EnPS-toluene, for the purpose of observing the effects of toluene dilution of the electrolyte solution of Working Example 1 (Mg-EnPS) and chlorine removal with $AgBF_4$. The EnPS-toluene was a sample in which EnPS and toluene were mixed in the same ratio as during preparation of the electrolyte solution of Working Example 2 (Mg-EnPS-toluene). All of the spectra were normalized on both the vertical axis and the horizontal axis based on the peak of the normal propyl end moiety (a in the chemical formula of EnPS illustrated in FIG. 9) in the EnPS that is considered to be the least susceptible to the influence of the coordination to Mg among the EnPS signals.

In FIG. 9, a comparison of the EnPS spectra and the EnPS-toluene spectra shows that the peak for the hydrogens (c and d in the chemical formula of EnPS illustrated in FIG. 9) closet to the EnPS oxygen of the EnPS-toluene has shifted to a higher field. From this it can be seen that by adding toluene the state of the EnPS changes. In view of this, when the Mg-EnPS and the Mg-EnPS-toluene spectra are compared, since the peak for the hydrogens (c and d in the chemical formula of EnPS illustrated in FIG. 9) closet to the EnPS oxygen of the Mg-EnPS-toluene has shifted to a slightly higher field, there is the possibility that some kind of change has also occurred in the bond with the magnesium due to the addition of the toluene.

Further, a comparison of the Mg-EnPS and the Mg-EnPS-$BF_4$ spectra shows that the Mg-EnPS-$BF_4$ peak has broadened. This can be thought to be due to the Mg-EnPS-$BF_4$ having a higher viscosity than the Mg-EnPS.

Figure 10:
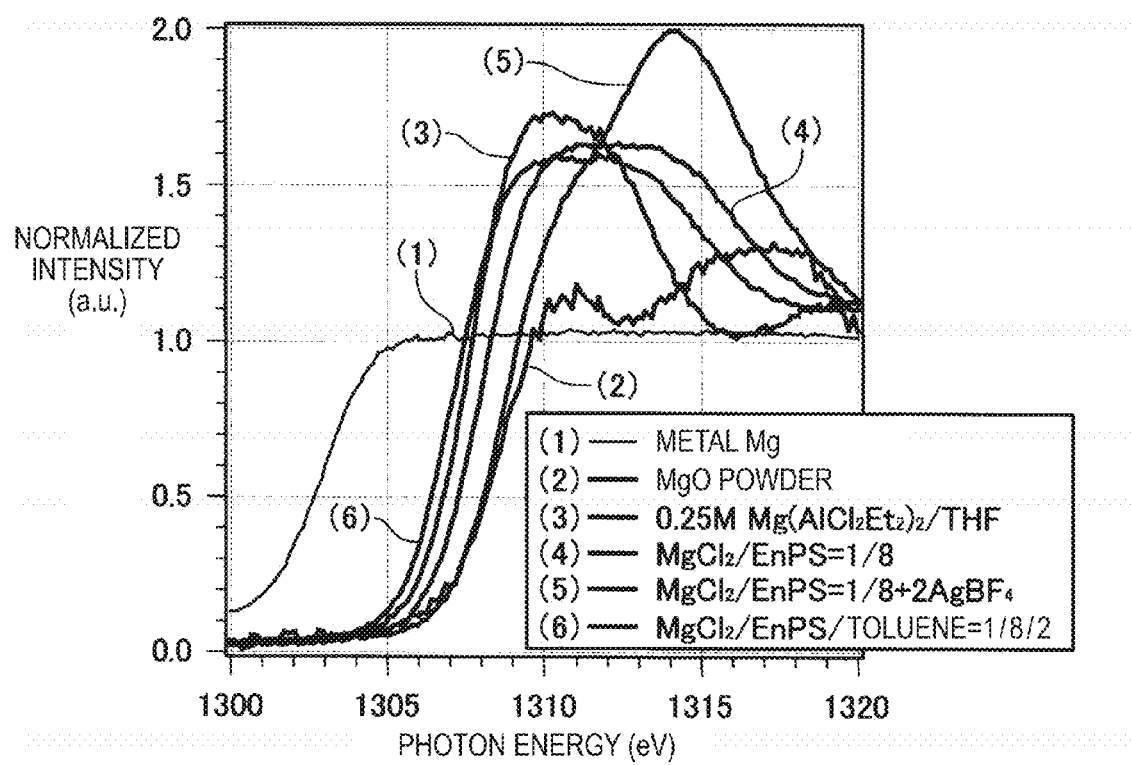
FIG. 10 is a line diagram illustrating the XANES spectra of the electrolyte solutions of Working Examples 1 to 3.
Figure 11:
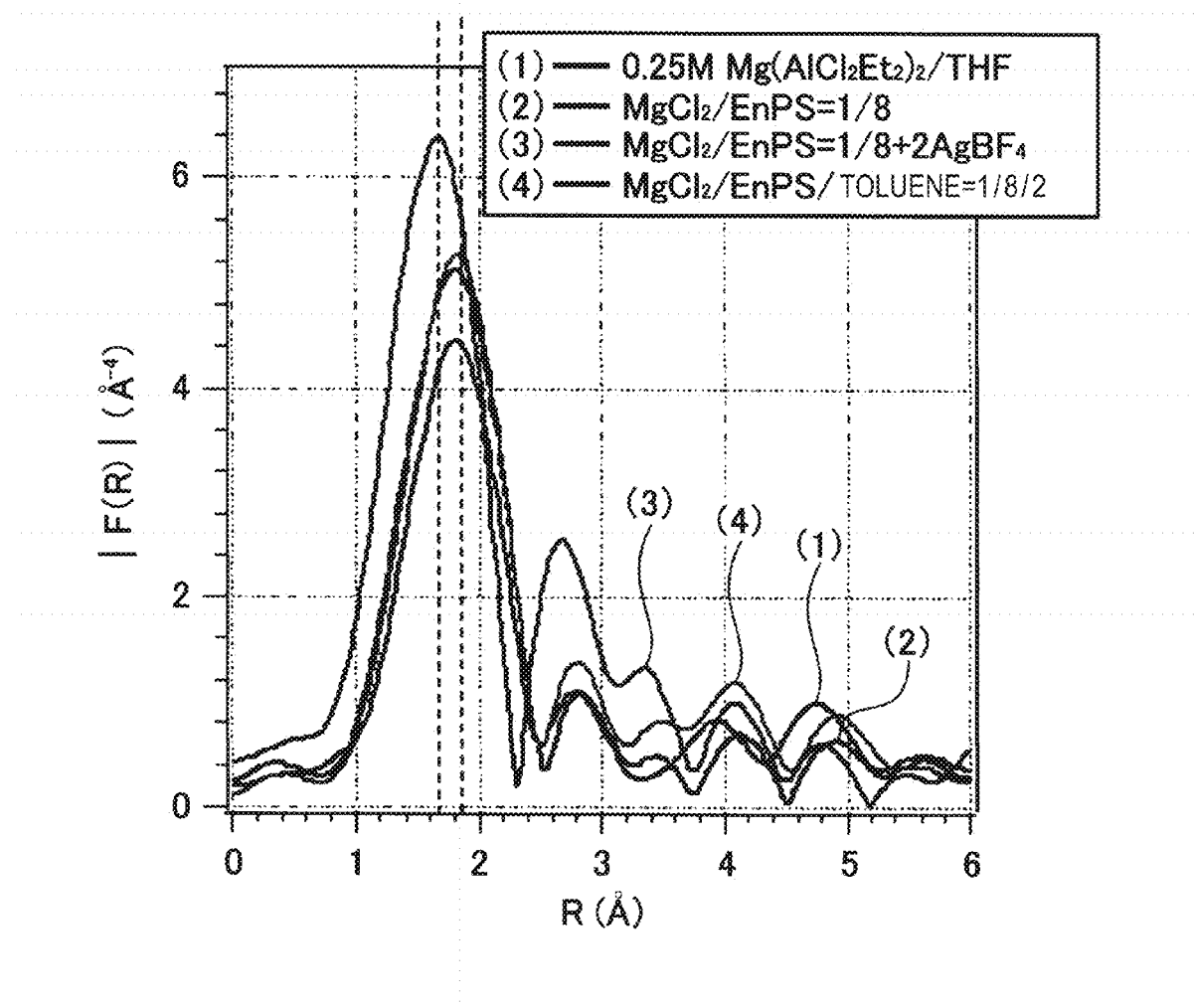
FIG. 11 is a line diagram illustrating a radial structure function of the electrolyte solutions of Working Examples 1 to 3.

FIG. 10 illustrates the XAFS (X-ray absorption fine structure) measurement results and the XANES spectra of the electrolyte solution of Working Example 1 (Mg-EnPS), the electrolyte solution of Working Example 2 (Mg-EnPS-toluene), and the electrolyte solution of Working Example 3 (Mg-EnPS-$BF_4$). Further, FIG. 11 illustrates a radial structure function |F(R)| (wherein R represents the distance from Mg), from which it can clearly be seen than the Mg in the Mg-EnPS and the Mg-EnPS-toluene has a four-coordinate dimer structure, and the Mg-EnPS-$BF_4$ has a six-coordinated monomer structure. The four-coordinate dimer structure and the six-coordinated monomer structure are as shown below (wherein L represents $Cl^-$ or EnPS).

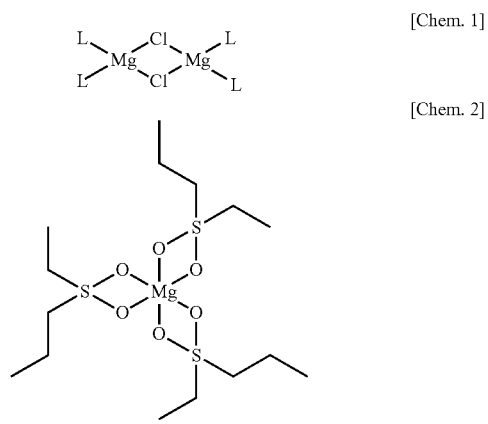

Figure 12:
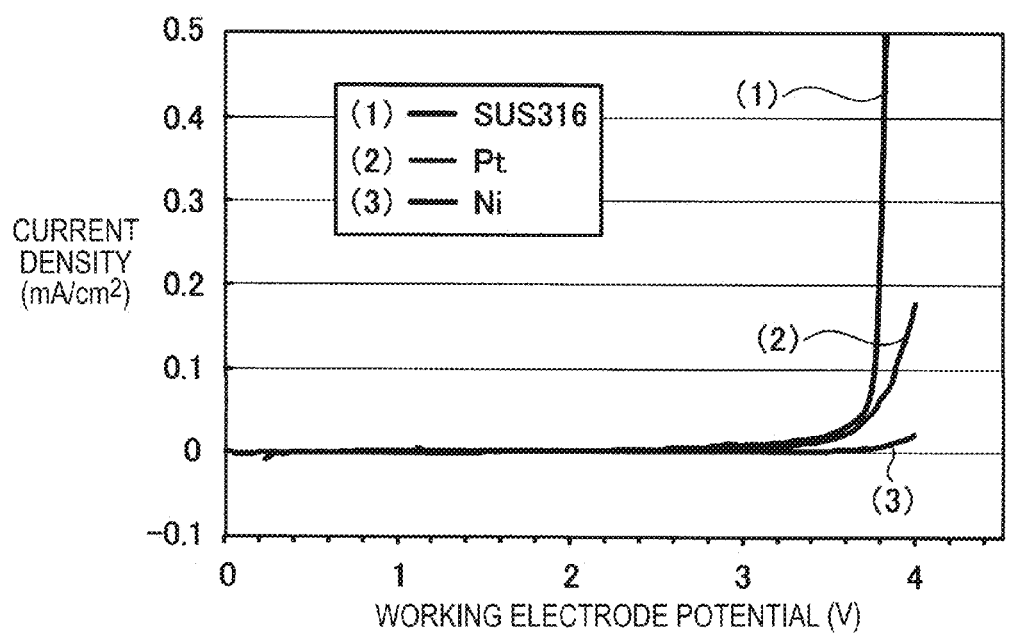
FIG. 12 is a graph illustrating a CV measurement result for examining the oxidative degradation potential of the electrolyte solution of Working Example 1 using three types of working electrode.

FIG. 12 illustrates the results of measuring the oxidative degradation potential of the electrolyte solution of Working Example 1 (Mg-EnPS) using three types of working electrode. The horizontal axis in FIG. 12 represents the potential of the working electrode with respect to Mg, and the vertical axis represents the current density. The three types of working electrode are stainless steel (SUS 316), platinum (Pt), and nickel (Ni). From FIG. 12, it can be seen that regardless of which of the three types of electrode is used, the oxidative degradation potential (3.6 V) is higher than the oxidative degradation potential (around 2.5 V) of past electrolyte solutions that use an ether solvent.

Figure 13:
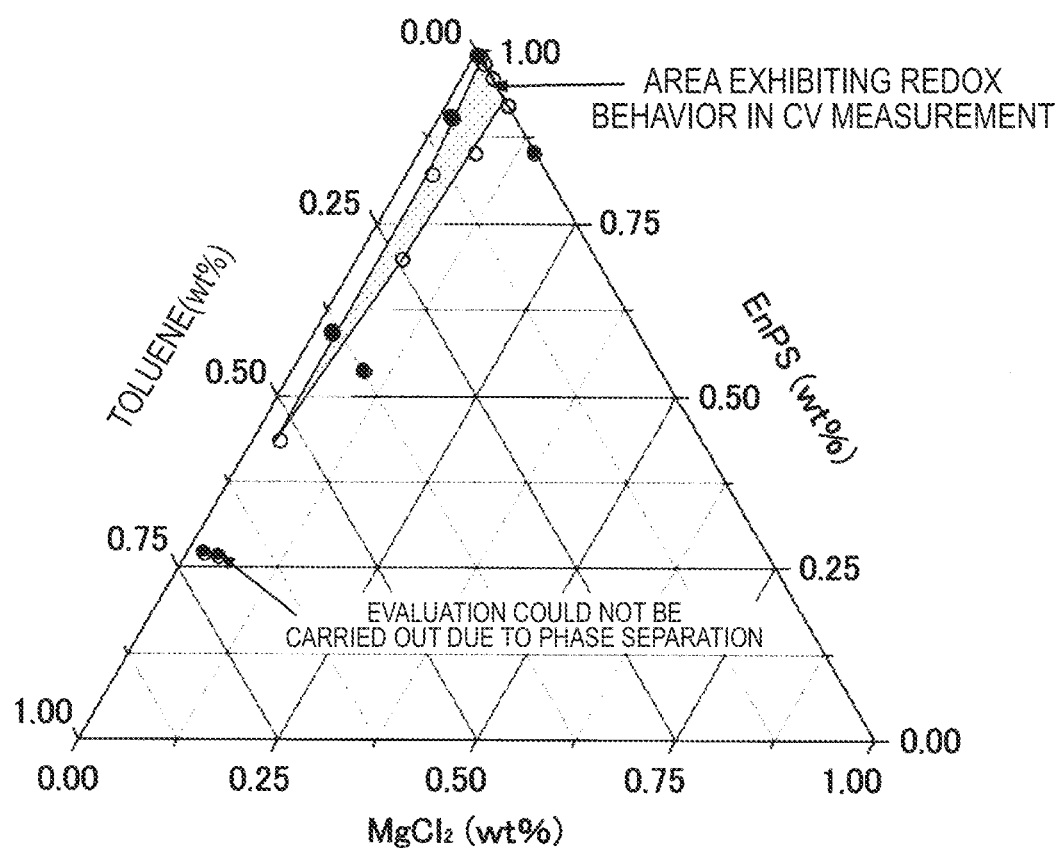
FIG. 13 is a line diagram illustrating a $MgCl_2$-EnPS-toluene three-dimensional phase diagram.

FIG. 13 illustrates a $MgCl_2$-EnPS-toluene three-dimensional phase diagram. In FIG. 13, the black circles and the white circles indicate the composition of the electrolyte solution samples on which the experiment was performed. The black circles are electrolyte solution samples that do not exhibit redox behavior in CV measurement, and the white circles are electrolyte solution samples that do exhibit redox behavior in CV measurement. It can be seen from these results that the dotted region in FIG. 13 is the region in which redox behavior is exhibited in CV measurement.

Working Example 4

A Mg electrolyte solution (Mg-EiPS) was prepared as follows.

Weighing of the reagents and the mixing operation were carried out in a glove box (Ar/dew point −80 to −90° C.). While stirring 100 mL of dehydrated methanol (manufactured by Nacalai Tesque, Inc.) with a stirrer, 3.81 g of anhydrous magnesium chloride (II) ($MgCl_2$) (manufactured by Sigma-Aldrich Co., LLC) was added. It was confirmed by measuring the external temperature of the reaction vessel with a contact thermometer (T2; manufactured by testo K.K.) that a slight amount of heat was produced when the $MgCl_2$ dissolved in the methanol. This heat is generated by the heat of reaction when the methanol coordinates to the Mg. The Mg in the methanol is thought to have a structure in which the methanol is coordinated to it. Further, there was a slight amount of white cloudiness after the dissolution of the $MgCl_2$ as well. This is thought to be due to the water present in the methanol reacting with the Mg to produce $Mg(OH)_2$. Since the white cloudiness was slight, synthesis was continued without filtering.

After dissolution of the $MgCl_2$, 43.6 g of EiPS was added while stirring with a stirrer.

The solution was removed from the glove box while maintaining a state in which air was prevented from mixing therein. Then, while reducing the pressure using a rotary pump (G-110D, manufactured by ULVAC Technologies, Inc.), the methanol was removed by heating and stirring at 110° C. for 2 hours. Although a white sediment was produced when the amount of methanol decreased, the produced sediment dissolved when the pressure reduction and heating were continued. This change in solubility is thought to be due to the exchange of the Mg ligands from methanol to EiPS. The removal of the methanol was confirmed by $^1$H NMR measurement.

Since the white cloudiness produced when the $MgCl_2$ dissolved in the methanol remained in the sample from which methanol had been removed, the sample was filtered (pore size 0.45 μm, manufactured by Whatman Ltd.) in a glove box.

The prepared electrolyte solution had a Mg:Cl:EiPS ratio of 1:2:8 (molar ratio) and a Mg concentration of 1.00 mol/L.

Working Example 5

A Mg electrolyte solution (Mg-DnPS) was prepared as follows.

Weighing of the reagents and the mixing operation were carried out in a glove box (Ar/dew point −80 to −90° C.). While stirring 100 mL of dehydrated methanol (manufactured by Nacalai Tesque, Inc.) with a stirrer, 3.81 g of anhydrous magnesium chloride (II) ($MgCl_2$) (manufactured by Sigma-Aldrich Co., LLC) was added. It was confirmed by measuring the external temperature of the reaction vessel with a contact thermometer (T2; manufactured by testo K.K.) that a slight amount of heat was produced when the $MgCl_2$ dissolved in the methanol. This heat is generated by the heat of reaction when the methanol coordinates to the Mg. The Mg in the methanol is thought to have a structure in which the methanol is coordinated to it. Further, there was a slight amount of white cloudiness after the dissolution of the $MgCl_2$ as well. This is thought to be due to the water present in the methanol reacting with the Mg to produce $Mg(OH)_2$. Since the white cloudiness was slight, synthesis was continued without filtering.

After dissolution of the $MgCl_2$, 48.1 g of DnPS that had been dissolved in advance using a hot stirrer was added while stirring with a stirrer.

The solution was removed from the glove box while maintaining a state in which air was prevented from mixing therein. Then, while reducing the pressure using a rotary pump (G-110D, manufactured by ULVAC Technologies, Inc.), the methanol was removed by heating and stirring at 120° C. for 2 hours. Although a white sediment was produced when the amount of methanol decreased, the produced sediment dissolved when the pressure reduction and heating were continued. This change in solubility is thought to be due to the exchange of the Mg ligands from methanol to DnPS. The removal of the methanol was confirmed by $^1$H NMR measurement.

Since the white cloudiness produced when the $MgCl_2$ dissolved in the methanol remained in the sample from which methanol had been removed, the sample was filtered (pore size 0.45 μm, manufactured by Whatman Ltd.) in a glove box.

The prepared electrolyte solution had a Mg:Cl:DnPS ratio of 1:2:8 (molar ratio).

Figure 14:
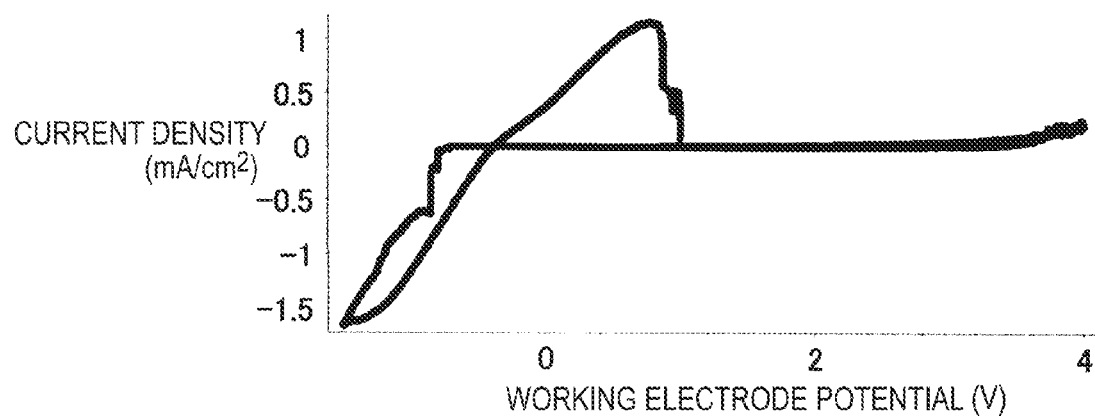
FIG. 14 is a graph illustrating a CV measurement result of the electrolyte solution of Working Example 4.
Figure 15:
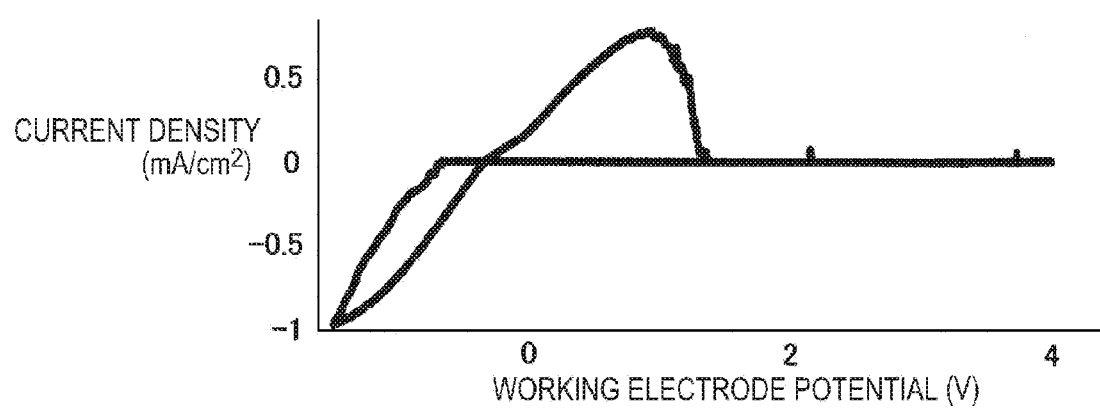
FIG. 15 is a graph illustrating a CV measurement result of the electrolyte solution of Working Example 5.

FIGS. 14 and 15 are graphs illustrating the CV measurement results of the electrolyte solution of Working Example 4 (Mg-EiPS) and the electrolyte solution of Working Example 5 (Mg-DnPS), respectively. From these graphs it can be seen that an electrolyte solution capable of reversibly dissolving and precipitating Mg can be prepared based on a composition from both the electrolyte solution of Working Example 4 (Mg-EiPS) and the electrolyte solution of Working Example 5 (Mg-DnPS).

Third Embodiment of the Present Disclosure

Magnesium Ion Battery

Next, a third embodiment of the present disclosure will be described. In the third embodiment of the present disclosure, a magnesium ion battery will be described that uses the electrolyte solution according to the first or second embodiment of the present disclosure as an electrolyte layer.

Figure 16:
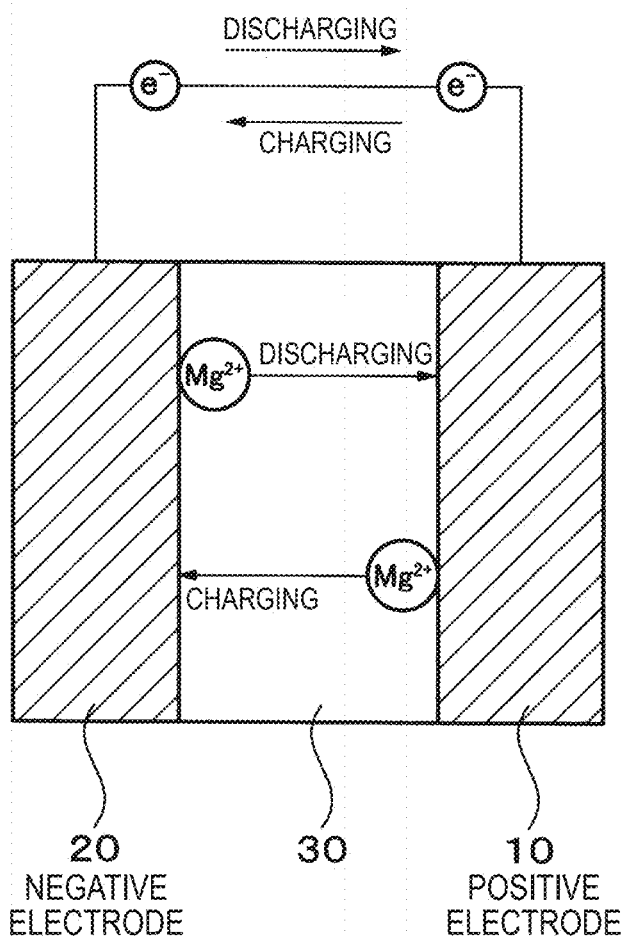
FIG. 16 is a line diagram illustrating a magnesium ion battery according to a third embodiment of the present disclosure.

FIG. 16 schematically illustrates the basic configuration of such a magnesium ion battery.

As illustrated in FIG. 16, this magnesium ion battery is configured from a positive electrode 10 and a negative electrode 20 that oppose each other across an electrolyte layer 30 formed from an electrolyte solution. Examples of positive electrode active materials that can be used for the positive electrode 10 include, but are not limited to, sulfur (S), graphite fluoride ($(CF)_n$), and an oxide or a halide of various metals (e.g., scandium (Sc), titanium (Ti), vanadium (V), chromium (Cr), manganese (Mn), iron (Fe), cobalt (Co), nickel (Ni), copper (Cu), zinc (Zn) etc.). As the negative electrode 20, magnesium metal alone or a magnesium alloy may be used, for example. Typically, the negative electrode 20 is formed in a sheet shape or a box shape. However, the shape is not limited to these. For example, the negative electrode 20 can be formed using a powder. As the electrolyte solution forming the electrolyte layer 30, the electrolyte solution according to the first or second embodiment of the present disclosure is used.

(Operation of the Magnesium Ion Battery)

In this magnesium ion battery, during charging, electrical energy is converted into chemical energy and stored by magnesium ions ($Mg^{2+}$) passing through the electrolyte layer 30 from the positive electrode 10 and moving to the negative electrode 20. During discharge, electrical energy is generated by magnesium ions passing through the electrolyte layer 30 from the negative electrode 20 and returning to the positive electrode 10.

Working Example 6

A coin battery was fabricated using magnesium (Mg) for the negative electrode, sulfur (S) for the positive electrode, and a $MgCl_2$/EnPS/toluene electrolyte solution prepared from $MgCl_2$/EnPS=⅛ (mol) and $MgCl_2$/toluene=¼ (wt.).

Figure 17:
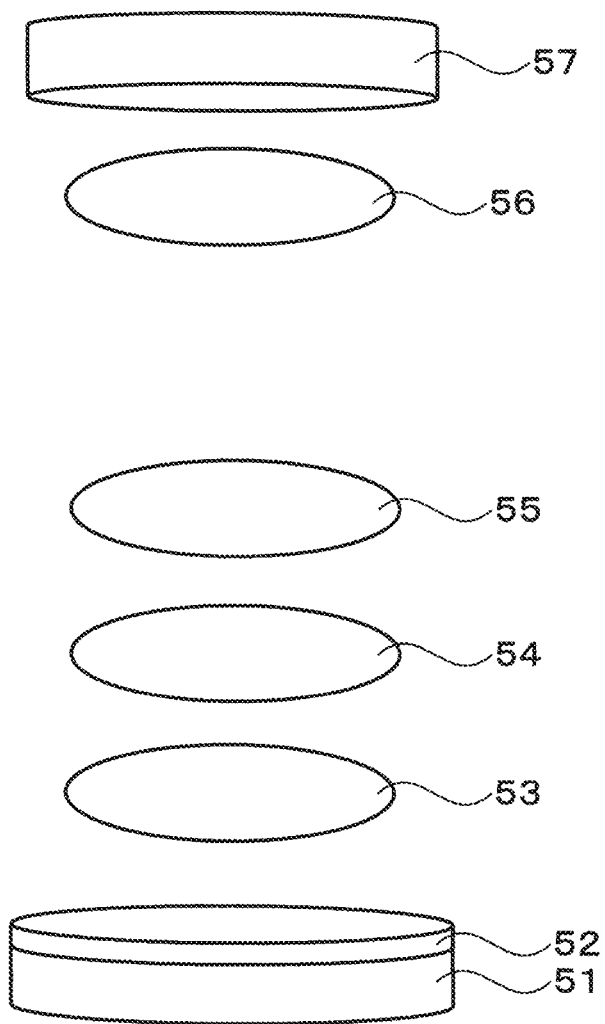
FIG. 17 is an exploded perspective diagram illustrating the configuration of the coin battery of Working Example 6.

The configuration of this coin battery is illustrated in FIG. 17. As illustrated in FIG. 17, a gasket 52 was placed on a coin battery can 51. A positive electrode 53 formed from sulfur, a separator 54 made from a glass filter, a negative electrode 55 formed from a 250 μm-thick Mg plate, a spacer 56 formed from a 500 μm-thick stainless steel plate, and a coin battery lid 57 were stacked in that order. Then, the coin battery can 51 was sealed. The spacer 56 had been spot-welded to the coin battery lid 57 in advance.

Figure 18:
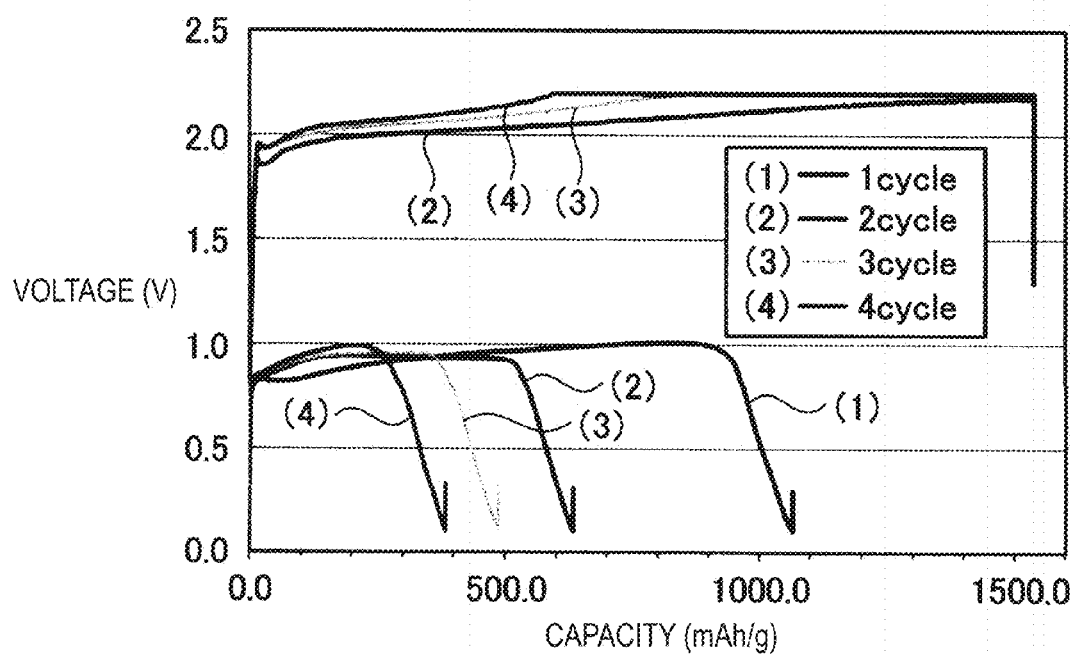
FIG. 18 is a line diagram illustrating a measurement result of the charge/discharge properties of the coin battery of Working Example 6.

The charge/discharge properties of this coin battery were measured. FIG. 18 illustrates those results. It can be seen from FIG. 18 that the cycle deterioration is smaller than the cycle deterioration of past electrolyte solutions (refer to Nature Communications Volume: 2, Article number: 427 DOI: doi:10.1038/ncomms1435) that use THF. This is thought to be due to differences in the solvent, namely, that sulfur does not easily dissolve in sulfone (sulfur dissolves in THF).

The elution of sulfur from the positive electrode formed from sulfur into the electrolyte solution was examined based on measurement of Raman scattering. The results are shown in Table 1.

TABLE 1

| | Peak position | | | |
|---|---|---|---|---|
| | 473 $cm^{-1}$ S Concentration (wt %) | 219 $cm^{-1}$ S Concentration (wt %) | 155 $cm^{-1}$ S Concentration (wt %) | Sulfur concentration (Average) |
| $MgCl_2$:EnPS = 1:8 | 0 | 0 | 0 | 0 |
| $MgCl_2$:EnPS:Toluene = 1:8:4 | 0 | 0 | 0 | 0 |

TABLE 1-continued

| | Peak position | | | |
|---|---|---|---|---|
| | 473 $cm^{-1}$ S Concentration (wt %) | 219 $cm^{-1}$ S Concentration (wt %) | 155 $cm^{-1}$ S Concentration (wt %) | Sulfur concentration (Average) |
| $Mg(AlCl_2 + Et2)$ - S | 1.85 | 1.80 | 1.91 | 1.85 [5] |
| THF - S | 1.88 | 1.69 | 1.79 | 1.79 [7] |
| Toluene - S | 1.58 | 1.79 | 1.62 | 1.66 [9] |

From Table 1, it can be seen that the solubility of sulfur in $MgCl_2$:EnPS:toluene=1:8:4 and $MgCl_2$:EnPS=1:8 was less than the detection limit of the Raman scattering measurement. In contrast, about 1.8 to 2 wt. % of the sulfur dissolves in 0.25 M $Mg(AlCl_2Et_2)$/THF.

Since sulfur dissolves in toluene, when a positive electrode made from sulfur is used, it is desirable that the electrolyte composition has a low toluene content, or that no toluene is included.

Figure 19:
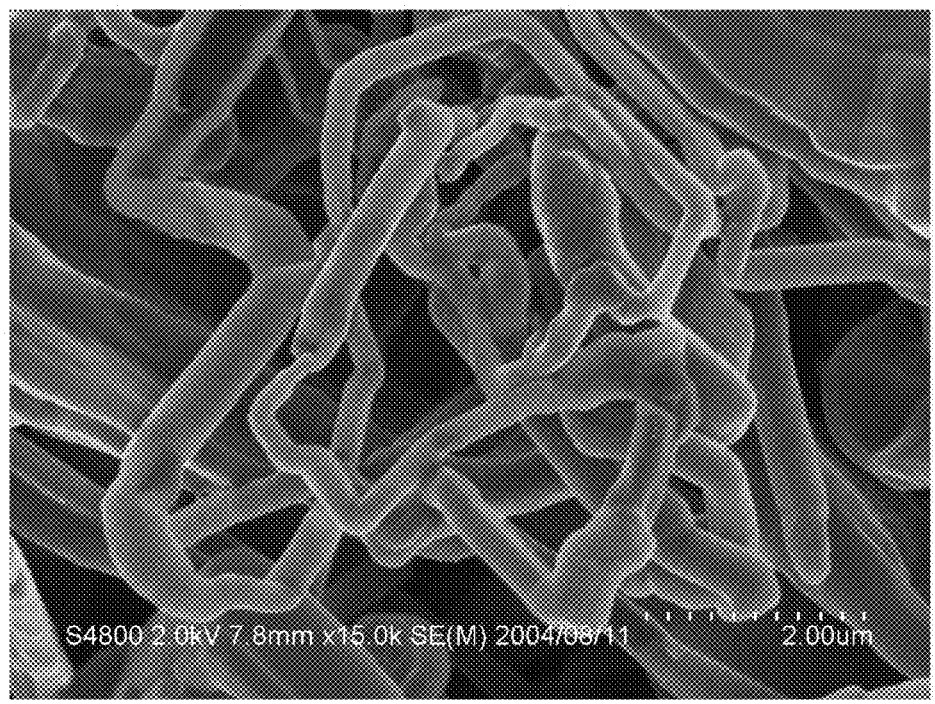
FIG. 19 is a photograph that shows a scanning electron micrograph of a sample of lithium metal that has precipitated on copper using a $LiPF_6$/EC-DMC electrolyte solution.
Figure 20:
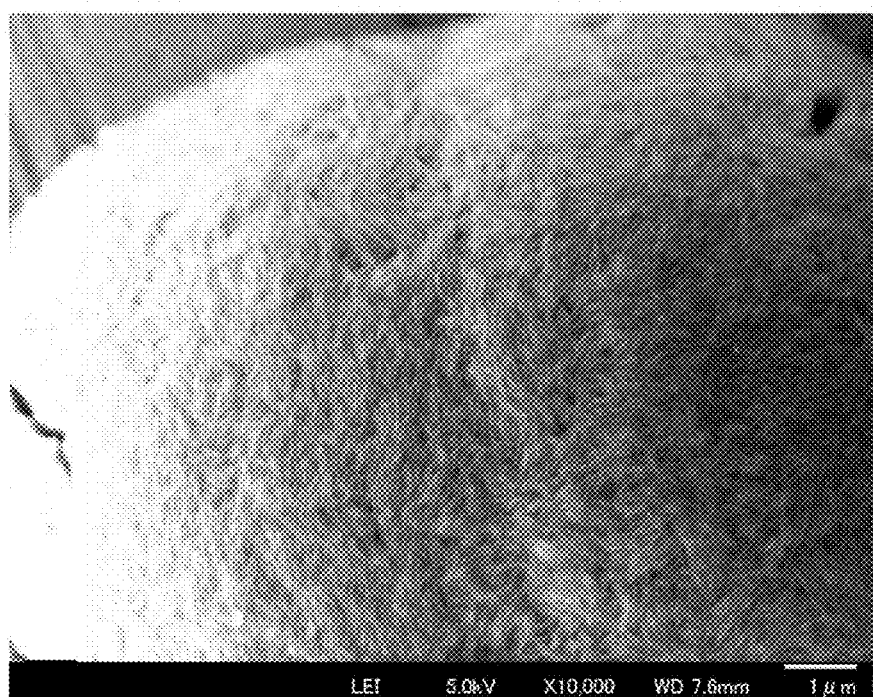
FIG. 20 is a photograph that shows a scanning electron micrograph of a sample of magnesium metal that has precipitated on copper using the electrolyte solution of Working Example 1.

Next, the results of investigating the precipitation modes of Mg will be described. FIG. 19 illustrates results obtained by capturing with a scanning electron microscope (SEM) an image of Li metal precipitated on a conducting body (e.g., Cu) on the negative electrode side when a $LiPF_6$/EC-DMC electrolyte solution is used. FIG. 20 illustrates results obtained by capturing with a scanning electron microscope (SEM) an image of Mg metal precipitated on Cu when a $MgCl_2$/EnPS electrolyte solution is used. From FIGS. 19 and 20, it can be seen that when Li metal is precipitated using a $LiPF_6$/EC-DMC electrolyte solution, dendrites form on the Cu, whereas when Mg metal is precipitated using a $MgCl_2$/EnPS electrolyte solution, dendrites do not form on the Cu. Based on this, it can be said that there is a chance that the problems of a Li metal negative electrode can be resolved with a Mg metal negative electrode.

According to this third embodiment of the present disclosure, a novel high-performance magnesium ion battery can be realized that uses an electrolyte solution in which a magnesium salt is dissolved in a sulfone, or an electrolyte solution in which a magnesium salt is dissolved in a solvent formed from a sulfone and a non-polar solvent.

This magnesium ion battery can be mounted as a drive power source or an auxiliary power source in, for example, a notebook-type personal computer, a PDA (a portable information terminal), a mobile phone, a cordless phone handset, a video movie recorder, a digital still camera, an e-book, an electronic dictionary, a portable music player, a radio, headphones, a game console, a navigation system, a memory card, a cardiac pacemakers, a hearing aid, an electric tool, an electric shaver, a refrigerator, an air conditioner, a television, a stereo, a water heater, a microwave oven, a dishwasher, a washing machine, a dryer, lighting equipment, toys, medical equipment, a robot, a load conditioner, traffic lights, a railroad wagon, a golf cart, an electric cart, an electric automobile (including a hybrid automobile), or as a power storage power source for buildings such as homes or power generation equipment. Alternatively, this magnesium ion battery can be used for supplying power to such devices. In an electric automobile, the conversion apparatus that converts power into a drive force based on the supply of power is usually a motor. Examples of the control apparatus for performing information processing relating to vehicle control include a control apparatus that displays the remaining battery level based on information relating to the remaining level of the battery. This magnesium ion battery can also be used as a storage apparatus in a so-called smart grid. This storage apparatus can store power by receiving a supply of power from another power source. Examples of other power sources that can be used include thermal power generation, nuclear power generation, hydroelectric power generation, solar power generation, wind power generation, geothermal power generation, a fuel cell (including a biofuel cell) and the like.

It should be understood by those skilled in the art that various modifications, combinations, sub-combinations and alterations may occur depending on design requirements and other factors insofar as they are within the scope of the appended claims or the equivalents thereof.

For example, the numerical values, structures, configurations, shapes, materials and the like mentioned in the above embodiments of the present disclosure and the working examples are merely examples which may be changed as appropriate to different numerical values, structures, configurations, shapes, materials and the like.

Additionally, the present technology may also be configured as below.

(1) An electrolyte solution including:
  a solvent formed from a sulfone; and
  a magnesium salt dissolved in the solvent.
(2) The electrolyte solution according to (1), wherein the electrolyte solution includes a magnesium complex having a four-coordinate dimer structure in which the sulfone is coordinated to magnesium.
(3) The electrolyte solution according to (1) or (2), wherein the sulfone is an alkyl sulfone or an alkyl sulfone derivative represented by $R_1R_2SO_2$ (wherein $R_1$ and $R_2$ represent an alkyl group).
(4) The electrolyte solution according to (3), wherein the alkyl sulfone is at least one selected from the group consisting of dimethyl sulfone, methyl ethyl sulfone, methyl-n-propyl sulfone, methyl-i-propyl sulfone, methyl-n-butyl sulfone, methyl-i-butyl sulfone, methyl-s-butyl sulfone, methyl-t-butyl sulfone, ethyl methyl sulfone, diethyl sulfone, ethyl-n-propyl sulfone, ethyl-i-propyl sulfone, ethyl-n-butyl sulfone, ethyl-i-butyl sulfone, ethyl-s-butyl sulfone, ethyl-t-butyl sulfone, di-n-propyl sulfone, di-i-propyl sulfone, n-propyl-n-butyl sulfone, n-butyl ethyl sulfone, i-butyl ethyl sulfone, s-butyl ethyl sulfone, and di-n-butyl sulfone, and the alkyl sulfone derivative is ethyl phenyl sulfone.
(5) The electrolyte solution according to any one of (1) to (4), wherein the magnesium salt includes at least one selected from the group consisting of magnesium chloride, magnesium bromide, magnesium iodide, magnesium perchlorate, magnesium tetrafluoroborate, magnesium hexafluorophosphate, magnesium hexafluoroarsenate, magnesium perfluoro alkyl sulfonate, and magnesium perfluoroalkylsulfonyl imidate.
(6) The electrolyte solution according to any one of (1) to (5), further including:
  a salt formed from a cation in which a metal ion is at least one atom or group of atoms selected from the group consisting of aluminum, beryllium, boron, gallium, indium, silicon, tin, titanium, chromium, iron, cobalt, and lanthanum, or a salt formed from at least one atom, organic group, or anion selected from the group consisting of hydrogen, an alkyl group, an alkenyl group, an aryl group, a benzyl group, an amide group, a fluoride ion, a chloride ion, a bromide ion, an iodide ion, a perchlorate ion, a tetrafluoroborate ion, a hexafluorophosphate ion, a hexafluoroarsenate ion, a perfluoroalkyl sulfonate ion, and a perfluoroalkylsulfonyl imide ion.
(7) A method for producing an electrolyte solution, the method including:
  dissolving a magnesium salt in a low-boiling-point solvent capable of dissolving a magnesium salt;
  dissolving a sulfone in a solution in which the magnesium salt is dissolved in the low-boiling-point solvent; and
  removing the low-boiling-point solvent from the solution in which the sulfone is dissolved.
(8) The method for producing an electrolyte solution according to (7), wherein the low-boiling-point solvent is an alcohol.
(9) An electrolyte solution including:
  a solvent formed from a sulfone and a non-polar solvent; and
  a magnesium salt dissolved in the solvent.
(10) The electrolyte solution according to (9), wherein the non-polar solvent is a non-aqueous solvent having a permittivity and a donor number that are both 20 or less.
(11) The electrolyte solution according to (9) or (10), wherein the non-polar solvent is at least one selected from the group consisting of an aromatic hydrocarbon, an ether, a ketone, an ester, and a chain carbonate ester.
(12) The electrolyte solution according to (11), wherein the aromatic hydrocarbon is toluene, benzene, o-xylene, m-xylene, p-xylene, or 1-methyl naphthalene, the ether is diethyl ether or tetrahydrofuran, the ketone is 4-methyl-2-pentanone, the ester is methyl acetate or ethyl acetate, and the chain carbonate ester is dimethyl carbonate, diethyl carbonate, or ethyl methyl carbonate.
(13) A method for producing an electrolyte solution, the method including:
  dissolving a magnesium salt in a low-boiling-point solvent capable of dissolving a magnesium salt;
  dissolving a sulfone in the solution in which the magnesium salt is dissolved in the low-boiling-point solvent;
  removing the low-boiling-point solvent from the solution in which the sulfone is dissolved; and
  mixing a non-polar solvent in the solution from which the low-boiling-point solvent was removed.
(14) The method for producing an electrolyte solution according to (13), wherein the low-boiling-point solvent is an alcohol.
(15) An electrochemical device including:
  an electrolyte solution,
  wherein the electrolyte solution is
  an electrolyte solution including a solvent formed from a sulfone and a magnesium salt dissolved in the solvent, or
  an electrolyte solution including a solvent formed from a sulfone and a non-polar solvent, and a magnesium salt dissolved in the solvent.
(16) The electrochemical device according to (15), wherein the electrochemical device is a magnesium-using battery, capacitor, sensor, or magnesium ion filter.
(17) The electrochemical device according to (16), wherein the battery is a secondary battery, an air battery, or a fuel cell.
(18) The electrochemical device according to (17), wherein the secondary battery is a magnesium ion battery that has the electrolyte solution as an electrolyte layer.

The present disclosure contains subject matter related to that disclosed in Japanese Priority Patent Application JP 2012-216811 filed in the Japan Patent Office on Sep. 28, 2012, the entire content of which is hereby incorporated by reference.

What is claimed is:

1. An electrolyte solution comprising:
   a solvent formed from a sulfone; and
   a magnesium salt dissolved in the solvent,
   wherein a molar ratio of the sulfone based on the magnesium salt in the electrolyte solution is 4 or more to 35 or less.

2. The electrolyte solution according to claim 1, wherein the electrolyte solution includes a magnesium complex having a four-coordinate dimer structure in which the sulfone is coordinated to magnesium.

3. The electrolyte solution according to claim 2, wherein the sulfone is an alkyl sulfone or an alkyl sulfone derivative represented by $R_1R_2SO_2$ (wherein $R_1$ and $R_2$ represent an alkyl group).

4. The electrolyte solution according to claim 3, wherein the alkyl sulfone is at least one selected from the group consisting of dimethyl sulfone, methyl ethyl sulfone, methyl-n-propyl sulfone, methyl-i-propyl sulfone, methyl-n-butyl sulfone, methyl-i-butyl sulfone, methyl-s-butyl sulfone, methyl-t-butyl sulfone, ethyl methyl sulfone, diethyl sulfone, ethyl-n-propyl sulfone, ethyl-i-propyl sulfone, ethyl-n-butyl sulfone, ethyl-i-butyl sulfone, ethyl-s-butyl sulfone, ethyl-t-butyl sulfone, di-n-propyl sulfone, di-i-propyl sulfone, n-propyl-n-butyl sulfone, n-butyl ethyl sulfone, i-butyl ethyl sulfone, s-butyl ethyl sulfone, and di-n-butyl sulfone, and the alkyl sulfone derivative is ethyl phenyl sulfone.

5. The electrolyte solution according to claim 4, wherein the magnesium salt includes at least one selected from the group consisting of magnesium chloride, magnesium bromide, magnesium iodide, magnesium perchlorate, magnesium tetrafluoroborate, magnesium hexafluorophosphate, magnesium hexafluoroarsenate, magnesium perfluoroalkyl sulfonate, and magnesium perfluoroalkylsulfonyl imidate.

6. The electrolyte solution according to claim 5, further comprising:
   a salt formed from a cation in which a metal ion is at least one atom or group of atoms selected from the group consisting of aluminum, beryllium, boron, gallium, indium, silicon, tin, titanium, chromium, iron, cobalt, and lanthanum, or a salt formed from at least one atom, organic group, or anion selected from the group consisting of hydrogen, an alkyl group, an alkenyl group, an aryl group, a benzyl group, an amide group, a fluoride ion, a chloride ion, a bromide ion, an iodide ion, a perchlorate ion, a tetrafluoroborate ion, a hexafluorophosphate ion, a hexafluoroarsenate ion, a perfluoroalkyl sulfonate ion, and a perfluoroalkylsulfonyl imide ion.

7. A method for producing an electrolyte solution, the method comprising:
   dissolving a magnesium salt in a low-boiling-point solvent capable of dissolving a magnesium salt;
   dissolving a sulfone in a solution in which the magnesium salt is dissolved in the low-boiling-point solvent; and
   removing the low-boiling-point solvent from the solution in which the sulfone is dissolved.

8. The method for producing an electrolyte solution according to claim 7, wherein the low-boiling-point solvent is an alcohol.

9. An electrolyte solution comprising:
   a solvent formed from a sulfone and a non-polar solvent; and
   a magnesium salt dissolved in the solvent,
   wherein a molar ratio of the sulfone based on the magnesium salt in the electrolyte solution is 4 or more to 20 or less.

10. The electrolyte solution according to claim 9, wherein the non-polar solvent is a non-aqueous solvent having a permittivity and a donor number that are both 20 and less.

11. The electrolyte solution according to claim 10, wherein the non-polar solvent is at least one selected from the group consisting of an aromatic hydrocarbon, an ether, a ketone, an ester, and a chain carbonate.

12. The electrolyte solution according to claim 11, wherein the aromatic hydrocarbon is toluene, benzene, o-xylene, m-xylene, p-xylene, or 1-methyl naphthalene, the ether is diethyl ether or tetrahydrofuran, the ketone is 4-methyl-2-pentanone, the ester is methyl acetate or ethyl acetate, and the chain carbonate is dimethyl carbonate, diethyl carbonate, or ethyl methyl carbonate.

13. A method for producing an electrolyte solution, the method comprising:
   dissolving a magnesium salt in a low-boiling-point solvent capable of dissolving a magnesium salt;
   dissolving a sulfone in a solution in which the magnesium salt is dissolved in the low-boiling-point solvent;
   removing the low-boiling-point solvent from the solution in which the sulfone is dissolved; and
   mixing a non-polar solvent in the solution from which the low-boiling-point solvent was removed.

14. The method for producing an electrolyte solution according to claim 13, wherein the low-boiling-point solvent is an alcohol.

15. An electrochemical device comprising:
   an electrolyte solution,
   wherein the electrolyte solution is
      a solution including a solvent formed from a sulfone and a magnesium salt dissolved in the solvent, wherein a molar ratio of the sulfone based on the magnesium salt in the electrolyte solution is 4 or more to 35 or less, or
      a solution including a solvent formed from a sulfone and a non-polar solvent, and a magnesium salt dissolved in the solvent, wherein a molar ratio of the sulfone based on the magnesium salt in the electrolyte solution is 4 or more to 20 or less.

16. The electrochemical device according to claim 15, wherein the electrochemical device is a magnesium-using battery, capacitor, sensor, or magnesium ion filter.

17. The electrochemical device according to claim 16, wherein the magnesium-using battery is a secondary battery, an air battery, or a fuel cell.

18. The electrochemical device according to claim 17, wherein the secondary battery is a magnesium ion battery that has the electrolyte solution as an electrolyte layer.

* * * * *